United States Patent [19]

Cozzi et al.

[11] Patent Number: 4,602,022

[45] Date of Patent: Jul. 22, 1986

[54] N-IMIDAZOLYL DERIVATIVES OF BICYCLIC COMPOUNDS

[75] Inventors: Paolo Cozzi; Germano Carganico; Antonio Pillan, all of Milan; Umberto Branzoli, Pavia, all of Italy

[73] Assignee: Farmitalia Carlo Erba, S.p.A., Milan, Italy

[21] Appl. No.: 673,722

[22] Filed: Nov. 21, 1984

Related U.S. Application Data

[62] Division of Ser. No. 510,358, Jul. 1, 1983, Pat. No. 4,510,149.

[30] Foreign Application Priority Data

Jul. 5, 1982 [GB] United Kingdom ............... 8219412

[51] Int. Cl.[4] .................. C07D 405/04; A61K 31/44
[52] U.S. Cl. ................................. 514/337; 514/382; 514/397; 548/250; 548/252; 548/336; 546/269
[58] Field of Search ............... 548/336, 252, 250; 546/269; 514/337, 382, 397

[56] References Cited

U.S. PATENT DOCUMENTS

| | | | |
|---|---|---|---|
| 3,485,917 | 12/1969 | Godefroi et al. | 514/400 |
| 3,541,109 | 6/1968 | Kaure | 548/346 |
| 3,637,731 | 7/1968 | Johnson | 548/346 |
| 4,006,243 | 2/1977 | Strehike | 548/346 |
| 4,342,775 | 8/1982 | Cozzi et al. | 514/422 |
| 4,492,707 | 1/1985 | Cozzi et al. | 548/346 |

FOREIGN PATENT DOCUMENTS

| | | |
|---|---|---|
| 827870 | 4/1974 | Belgium . |
| 887766 | 3/1981 | Belgium . |
| 893917 | 7/1981 | Belgium . |
| 951 | 8/1977 | European Pat. Off. . |
| 73663 | 8/1981 | European Pat. Off. . |
| 081566 | 7/1981 | Japan . |
| 6705095 | 10/1967 | Netherlands . |

*Primary Examiner*—Jane T. Fan
*Attorney, Agent, or Firm*—Murray and Whisenhunt

[57] ABSTRACT

Compounds of the formula (I)

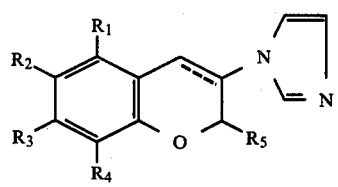

wherein
the symbol -------- represents a single or a double bond;
each of $R_1$, $R_2$, $R_3$ and $R_4$, which may be the same or different is
(a) hydrogen; hydroxy; halogen; cyano; $C_1$–$C_6$ alkyl; $C_1$–$C_6$ alkoxy; a $C_2$–$C_4$ acyl or $C_2$–$C_4$ acylamino group; —SR', —N(R')(R''), —CH$_2$OR', —COR or —CH$_2$COR, wherein R is OR' or —N(R')(R'') and each of R' and R'', being the same or different, is hydrogen or $C_1$–$C_6$ alkyl; or
(b) one of $R_1$, $R_2$, $R_3$ and $R_4$ is 5-tetrazolyl or a group selected from —COCH$_2$OR', —CH=C(R')—COR and —X—C(R')(R'')—COR, wherein R, R' and R'' are as defined above, and X is —O—, —S—, or —NH—, and the others are as defined above under (a);
$R_5$ is hydrogen, $C_1$–$C_6$ alkyl, $C_3$–$C_6$ cycloalkyl, or a phenyl or 3-pyridyl ring, wherein the phenyl or pyridyl ring is unsubstituted or substituted by one to three substituents chosen from hydroxy and $C_1$–$C_4$ alkoxy; or pharmaceutically acceptable salt thereof exhibit pharmaceutical activity as vasodilators or blood platelet aggregation inhibitors. Additionally, these compounds and their pharmaceutically acceptable salts are useful in the treatment of migraine, diabetic microangiopathy, rheumatoid arthritis, hypertension, peptic ulcers, osteoporosis, angina pectoris, atherosclerosis and dislipidaemies.

18 Claims, No Drawings

N-IMIDAZOLYL DERIVATIVES OF BICYCLIC COMPOUNDS

This is a Divisional application of Ser. No. 510,358, filed July 1, 1983, now U.S. Pat. No. 4,510,149.

The present invention relates to a new N-imidazolyl derivatives of bicyclic compounds, in particular to N-imidazolyl derivatives of 3,4-dihydro-2H-1-benzopyran, 2H-1-benzopyran, 1,2,3,4-tetrahydronaphthalene, 1,2-dihydronaphthalene, indane and indene, to a process for their preparation and to pharmaceutical compositions containing them.

It is known that some compounds having an imidazole skeleton, for example, imidazole itself, 1-alkylimidazoles, and 1-(2-isopropylphenyl)-imidazole derivatives are able to inhibit thromboxane $A_2$ ($TXA_2$) synthetase, [Prostaglandins, vol. 13, No. 4, 611 (1977); Biochemical and Biophysical Research Communications, vol. 80, No. 1, 236 (1978)].

However, since imidazole and 1-lower alkylimidazoles show only a very weak $TXA_2$ inhibiting effect, these compounds are devoid of any practical utility as medicines. Therefore, it is very important to obtain compounds possessing a stronger and more specific inhibitory effect on $TXA_2$ synthetase.

Recently other imidazolyl compounds were synthetized, and exactly N-imidazolyl derivatives of 1-chroman (U.S. Pat. No. 4,342,775) and N-imidazolyl derivatives of 1,2,3,4-tetrahydro-naphthalene, indane and 2-substituted-1-chroman (UK published patent application No. 2,106,509 A), which are endowed with a strong blood platelet-antiaggregating activity, but do not possess any activity as inhibitors of $TXA_2$ synthetase. Surprisingly, it has now been found that certain imidazolyl derivatives, although structurally related to those described in U.S. Pat. No. 4,342,775 and in UK published patent application No. 2,106,509 A, are strong selective inhibitors of $TXA_2$ synthesis and furthermore stimulators of $PGI_2$ synthesis. These compounds are described in the present invention, which, furthermore, provides some imidazolyl-derivatives endowed with a strong hypolipaemic activity, but with no activity on the $TXA_2/PGI_2$ system. More exactly the invention provides compounds having the following general formula (I)

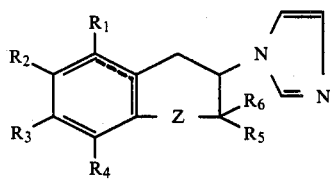
(I)

wherein
the symbol ———— represents a single or a double bond;

Z completes a single bond or is an oxygen atom or a —$CH_2$— group;

each of $R_1$, $R_2$, $R_3$ and $R_4$, which may be the same or different, is
(a) hydrogen; hydroxy; halogen; cyano; $C_1$-$C_6$ alkyl; $C_1$-$C_6$ alkoxy; a $C_2$-$C_4$ acyl or $C_2$-$C_4$ acylamino group; —SR',

—$CH_2OR'$, —$COR$ or —$CH_2COR$, wherein R is —OR' or

and each of R' and R", being the same or different, is hydrogen or $C_1$-$C_6$ alkyl; or
(b) one of $R_1$, $R_2$, $R_3$ and $R_4$ is 5-tetrazolyl or a group selected from —$COCH_2OR'$,

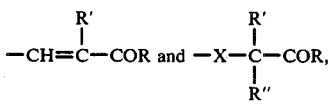

wherein R, R' and R" are as defined above, and X is —O—, —S— or —NH—, and the others are as defined above under (a);

one of $R_5$ and $R_6$ is hydrogen and the other is hydrogen, $C_1$-$C_6$ alkyl, $C_3$-$C_6$ cycloalkyl, or a phenyl or pyridyl ring, wherein the phenyl or pyridyl ring is unsubstituted or substituted by one to three substituents chosen from hydroxy and $C_1$-$C_4$ alkoxy; and the pharmaceutically acceptable salts thereof.

The present invention includes all the possible isomers (e.g. cis and trans isomers and optical isomers) of the compounds of formula (I) and their mixtures, and the metabolites and the metabolic precursors of the compounds of formula (I).

The numbering used to identify the positions in the compounds of formula (I) is the conventional one, as is depicted in the following examples:

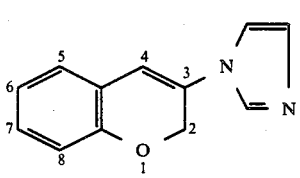
(1)

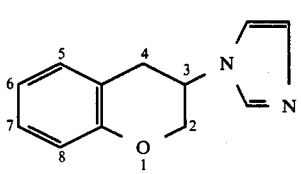
(2)

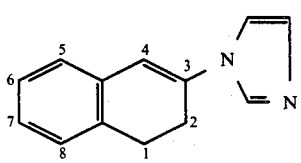
(3)

(4)

(5)

(6)

Pharmaceutically acceptable salts of the compounds of formula (I) include acid addition salts, with inorganic, e.g. nitric, hydrochloric, hydrobromic, sulphuric, perchloric and phosphoric, acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethylamine. The alkyl, alkoxy and alkylthio groups may be branched or straight chain groups.

A halogen atom is, for example, fluorine, chlorine or bromine, preferably chlorine or bromine.

A $C_1$–$C_6$ alkyl group is preferably a $C_1$–$C_4$ alkyl group.

A $C_1$–$C_6$ alkoxy group is preferably a $C_1$–$C_4$ alkoxy group, in particular methoxy, ethoxy or isopropoxy.

The term acyl, in $C_2$–$C_4$ acyl and $C_2$–$C_4$ acylamino groups, refers to acyl groups derived from both saturated and unsaturated carboxylic acids, preferably alkanoic acids, e.g. acetyl, propionyl and butyryl.

A $C_3$–$C_6$ cycloalkyl ring is preferably cyclopropyl or cyclohexyl, in particular cyclopropyl.

When one or more or $R_1$, $R_2$, $R_3$ and $R_4$ is halogen it is preferably chlorine or bromine.

When one or more of $R_1$, $R_2$, $R_3$ and $R_4$ is $C_1$–$C_6$ alkyl, it is preferably methyl, ethyl, isopropyl or tert.butyl.

When one or more of $R_1$, $R_2$, $R_3$ and $R_4$ is $C_2$–$C_4$ acyl, it is preferably acetyl or propionyl.

When one or more or $R_1$, $R_2$, $R_3$ and $R_4$ is $C_2$–$C_4$ acylamino, it is preferably acetylamino or propionylamino.

When R' and/or R" is $C_1$–$C_6$ alkyl, it is preferably $C_1$–$C_4$-alkyl, in particular methyl or ethyl.

When one of $R_1$, $R_2$, $R_3$ and $R_4$ is —COCH$_2$OR', it is preferably —COCH$_2$OH or —COCH$_2$O($C_1$–$C_4$)alkyl, in particular —COCH$_2$OCH$_3$ or —COCH$_2$OC$_2$H$_5$.

When one or more of $R_1$, $R_2$, $R_3$ and $R_4$ is —SR', it is e.g. —SH or —S($C_1$–$C_4$)alkyl, in particular methylthio; ethylthio or isopropylthio.

When one or more of $R_1$, $R_2$, $R_3$ and $R_4$ is $$-N\begin{matrix}R'\\R''\end{matrix}$$, it is preferably —NH$_2$, —NHCH$_3$, —NHC$_2$H$_5$, —N(CH$_3$)$_2$ or —N(C$_2$H$_5$)$_2$. When one or more of $R_1$, $R_2$, $R_3$ and $R_4$ is —CH$_2$OR', it is preferably —CH$_2$OH, —CH$_2$OCH$_3$ or —CH$_2$OC$_2$H$_5$.

When one or more of $R_1$, $R_2$, $R_3$ and $R_4$ is —COR, it is preferably carboxy or $C_1$–$C_4$ alkoxy-carbonyl, in particular methoxy-carbonyl or ethoxy-carbonyl, or it is amino-carbonyl or di($C_1$–$C_4$ alkyl)amino-carbonyl, in particular dimethylamino-carbonyl or diethylamino-carbonyl.

When one or more of $R_1$, $R_2$, $R_3$ and $R_4$ is —CH$_2$COR, it is preferably carboxymethyl or $C_1$–$C_4$ alkoxy-carbonylmethyl, in particular methoxy-carbonylmethyl or ethoxycarbonylmethyl or it is aminocarbonylmethyl or di($C_1$–$C_4$)alkyl-aminocarbonylmethyl, in particular dimethylaminocarbonylmethyl or diethylaminocarbonylmethyl.

When one of $R_1$, $R_2$, $R_3$ and $R_4$ is $$-X-\underset{R''}{\overset{R'}{C}}-COR,$$

it is preferably $$-O-\underset{R''}{\overset{R'}{C}}-COR,$$

wherein R' and R", being the same or different, are hydrogen, methyl or ethyl and R is hydroxy, $C_1$–$C_4$alkoxy, preferably methoxy or ethoxy, or R is amino or $C_1$–$C_4$alkylamino, in particular, methylamino or ethylamino, or it is di($C_1$–$C_4$)akylamino, in particular dimethylamino or diethylamino.

When one of $R_1$, $R_2$, $R_3$ and $R_4$ is $$-CH=\underset{}{\overset{R'}{C}}-COR,$$

R' is preferably hydrogen, methyl or ethyl and R is preferably hydroxy, methoxy, ethoxy, amino, methylamino ethylamino, dimethylamino or diethylamino.

When $R_5$ or $R_5$ is $C_1$–$C_6$ alkyl, it is preferably $C_1$–$C_4$alkyl, in particular methyl or ethyl.

When $R_5$ or $R_6$ is $C_3$–$C_6$ cyclolkyl, it is preferably cyclopropyl.

When $R_5$ or $R_6$ is a phenyl or a pyridyl ring, said ring is preferably unsubstituted, or when substituted, it is preferably substituted by one to three substituents chosen from hydroxy and $C_1$–$C_3$ alkoxy, in particular methoxy.

Preferred compounds of the invention are the compounds of formula (I) wherein the symbol ----- represents a double bond;
Z is as defined above;
each of $R_1$, $R_2$, $R_3$ and $R_4$, which may be the same or different, is
(a') hydrogen, hydroxy, halogen, $C_1$–$C_4$ alkyl, $C_1$–$C_4$ alkoxy, —CH$_2$OH, —COOR$_a$ or

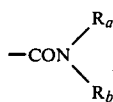

wherein each of $R_a$ and $R_b$ is independently hydrogen, or $C_1$-$C_4$ alkyl; or (b') one of $R_1$, $R_2$, $R_3$ and $R_4$ is $C_2$-$C_4$ acyl, —CH$_2$COOR$_a$,

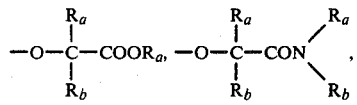

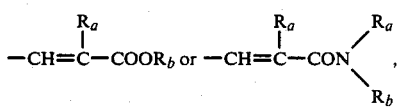

wherein $R_a$ and $R_b$ are as defined above, and the others are as defined above under (a');

one of $R_5$ and $R_6$ is hydrogen and the other is hydrogen, $C_1$-$C_3$ alkyl, cyclopropyl, or a phenyl or pyridyl ring unsubstituted or substituted by one to three substituents chosen from hydroxy and $C_1$-$C_2$ alkoxy; and the pharmaceutically acceptable salts thereof.

More preferred compounds of the invention are the compounds of formula (I) wherein
the symbol represents a double bond;
Z is an oxygen atom or a —CH$_2$— group;
one of $R_1$, $R_2$, $R_3$ and $R_4$ is —COOR$_a$, wherein $R_a$ is as defined above, and the others are independently chosen from hydrogen and hydroxy;
or one of $R_1$, $R_2$, $R_3$ and $R_4$ is —CONH$_2$OH, —COCH$_3$, —CH$_2$COOR$_a$,

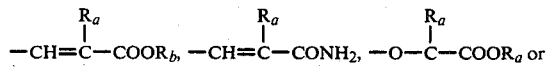

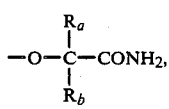

wherein $R_a$ and $R_b$ are as defined above, and the others are hydrogen;
$R_5$ and $R_6$ are both hydrogen; and the pharmaceutically acceptable salts thereof.

Particularly preferred compounds of the invention are the compounds of formula (I) wherein
the symbol ------- represents a double bond;
Z is oxygen or a —CH$_2$— group;
one of $R_1$, $R_2$, $R_3$ and $R_4$ is

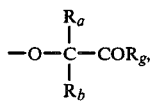

wherein $R_g$ is 13 NH$_2$ or —OR$_a$ and $R_a$ and $R_b$ are as defined above, and the others are hydrogen;
$R_5$ and $R_6$ are hydrogen; and the pharmaceutically acceptable salts thereof.

Particularly preferred compounds of the invention are also the compounds of formula (I), wherein the symbol represents a double bond;
z is a —CH$_2$— group;
one of $R_1$, $R_2$, $R_3$ and $R_4$ is —COR$_g$, —CH$_2$—COOR$_a$ or

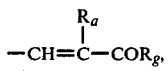

wherein $R_a$ and $R_g$ are as defined above, and the others are independently chosen from hydrogen and hydroxy;
$R_5$ and $R_6$ are hydrogen; and the pharmaceutically acceptable salts thereof.

Among the particularly preferred compounds of the invention, the most preferred are the compounds of formula (I), wherein
the symbol represents a double bond;
Z is a —CH$_2$— group;
one of $R_1$, $R_2$, $R_3$ and $R_4$ is —COR$_g$, wheerein $R_g$ is as defined above and the others are hydrogen;
$R_5$ and $R_6$ are hydrogen; and the pharmaceutically acceptable salts thereof.

Examples of preferred compounds of the invention are the following:
(1) 3-(1-imidazolyl)-2H-1-benzopyran;
(2) 3-(1-imidazolyl)-6-chloro-2H-1-benzopyran;
(3) 3-(1-imidazolyl)-6-methoxy-2H-1-benzopyran;
(4) 3-(1-imidazolyl)-6-carboxy-2H-1-benzopyran;
(5) 3-(1-imidazoly)-6-(2-carboxyisopropoxy)-2H-1-benzopyran;
(6) 3-(1-imidazolyl)-6-(2-carboxyvinyl)-2H-1-benzopyran;
(7) 2-methyl-3-(1-imidazolyl)-6-methoxy-2H-1-benzopyran;
(8) 2-methyl-3-(1-imidazolyl)-6-carboxy-2H-1-benzopyran;
(9) 2-methyl-3-(1-imidazolyl)-7-carboxy-2H-1-benzopyran;
(10) 2-methyl-3-(1-imidazolyl)-6-carbamoyl-2H-1-benzopyran;
(11) 2-methyl-3-(1-imidazolyl)-6-(2-carboxyvinyl)-2H-1-benzopyran;
(12) 2-methyl-3-(1-imidazolyl)-6-(2-carboxyisopropoxy)-2H-1-benzopyran;
(13) 2-isopropyl -3-(1-imidazolyl)-6-carboxy-2H-1-benzopyran;
(14) 2-methyl-3-(1-imidazolyl-6-ethoxycarbonyl-2H-1-benzopyran;
(15) 2-cyclopropyl-3-(1-imidazolyl)-b 6-carboxy-2H-1-benzopyran;
(16) 2-(3,4-dimethoxyphenyl)-3-(1-imidazolyl)-6-methoxy-2H-1-benzopyran;
(ʃ) 2-(3,4-dihydroxyphenyl)-3-(1-imidazolyl)-6-hydroxy-2H-1-benzopyran;
(18) 2-(3-pyridyl)-3-(1-imidazolyl)-6-carboxy-2H-1-benzopyran;
(19) 2-(4-hydroxyphenyl)-3-(1-imidazolyl)-5,7-dihydroxy-2H-1-benzopyran;
(20) 3,4-dihydro-3-(1-imidazolyl)-6-carboxyl-1-benzopyran;
(21) 3,4-dihydro-2-methyl-3-(1-imidazolyl)-6-carboxy-1-benzopyran;
(22) 3,4-dihydro-2-methyl-3-(1-imidazolyl)-6-(2-carboxyvinyl)-1-benzopyran;
(23) 1,2-dihydro-3-(1-imidazolyl)-naphthalene;
(24) 1,2-dihydro-3-(1-imidazolyl)-6-methoxynaphthalene;

(25) 1,2-dihydro-3-(1-imidazolyl)-7-methoxynaphthalene;
(26) 1,2-dihydro-3-(1-imidazolyl)-6-methoxy-7-bromonaphthalene;
(27) 1,2-dihydro-3-(1-imidazolyl)-8-methoxynaphthalene;
(28) 1,2-dihydro-3-(1-imidazolyl)-6-carboxynaphthalene;
(29) 1,2-dihydro-3-(1-imidazolyl)-6-carbamoylnaphthalene;
(30) 1,2-dihydro-3-(1-imidazolyl)-6-ethoxycarbonylnaphthalene;
(31) 1,2-dihydro-3-(1-imidazolyl)-6-hydroxymethylnaphthalene;
(32) 1,2-dihydro-3-(1-imidazolyl)-7-carboxynaphthalene;
(33) 1,2-adihydro-3-(1-imidazolyl)-5-carboxynaphthalene;
(34) 1,2-dihydro-3-(1-imidazolyl)-5-carbamoylnaphthalene;
(35) 1,2-dihydro-3-(1-imidazolyl)-6-ethoxycarbonylmethyloxynaphthalene;
(36) 1,2-dihydro-3-(1-imidazolyl)-6-(2-ethoxycarbonylisopropoxy)-naphthalene;
(37) 1,2-dihydro-3-(1-imidazolyl)-6-carboxymethyloxynaphthalene;
(38) 1,2-dihydro-3-(1-imidazolyl)-6-(2-carboxyisopropoxy)-naphthalene;
(39) 1,2-dihydro-3-(1-imidazolyl)-6-(2-carboxyvinyl)-naphthalene;
(40) 1,2-dihydro-3-(1-imidazolyl)-6-(2-ethoxycarbonylvinyl)-naphthalene;
(41) 1,2-dihydro-3-(1-imidazolyl)-6-hydroxy-7-acetylnaphthalene;
(42) 1,2-dihydro-3-(1-imidazolyl)-6-hydroxy-7-carboxynaphthalene;
(43) 1,2-dihydro-3-(1-imidazolyl)-6-tert-butyl-7-hydroxynaphthalene;
(44) 1,2-dihydro-3-(1-imidazolyl)-6-carboxymethylnaphthalene;
(45) 1,2-dihydro-3-(1-imidazolyl)-8-carboxynaphthalene;
(46) 1,2,3,4-tetrahydro-2-(1-imidazolyl)-7-carboxynaphthalene;
(47) 1,2,3,4-tetrahydro-2-(1-imidazolyl)-6-carboxynaphthalene;
(48) 1,2,3,4-tetrahydro-2-(1-imidazolyl)-7-(2-carboxyvinyl)-naphthalene;
(49) 2-(1-imidazolyl)-5-carboxyindene, and
(50) 2-(1-imidazolyl)-5-(2-carboxyvinyl)indene,
the pharmaceutically acceptable salts thereof and, when appropriate, the $C_1$–$C_4$ alkyl esters thereof.

The structural formulae of the above numbered compounds, indicated according to their progressive number, are reported in the following Table:

| Comp | Z | $R_1$ | $R_2$ | $R_3$ | $R_4$ | $R_5$ | $R_6$ | |
|---|---|---|---|---|---|---|---|---|
| 1 | —O— | H | H | H | H | H | H | double bond |
| 2 | —O— | H | Cl | H | H | H | H | double bond |
| 3 | —O— | H | $OCH_3$ | H | H | H | H | double bond |
| 4 | —O— | H | COOH | H | H | H | H | double bond |
| 5 | —O— | H | O—C($CH_3$)($CH_3$)—COOH | H | H | H | H | double bond |
| 6 | —O— | H | CH=CH—COOH | H | H | H | H | double bond |
| 7 | —O— | H | $OCH_3$ | H | H | H | $CH_3$ | double bond |
| 8 | —O— | H | COOH | H | H | H | $CH_3$ | double bond |
| 9 | —O— | H | H | COOH | H | H | $CH_3$ | double bond |
| 10 | —O— | H | $CONH_2$ | H | H | H | $CH_3$ | double bond |
| 11 | —O— | H | CH=CH—COOH | H | H | H | $CH_3$ | double bond |
| 12 | —O— | H | O—C($CH_3$)($CH_3$)—COOH | H | H | H | $CH_3$ | double bond |
| 13 | —O— | H | COOH | H | H | H | i-Pr | double bond |
| 14 | —O— | H | COOEt | H | H | H | $CH_3$ | double bond |
| 15 | —O— | H | COOH | H | H | H | cy-Pr | double bond |
| 16 | —O— | H | $OCH_3$ | H | H | H | Ph(3,4-$OCH_3$) | double bond |
| 17 | —O— | H | OH | H | H | H | Ph(3,4-OH) | double bond |
| 18 | —O— | H | COOH | H | H | H | 3-Py | double bond |
| 19 | —O— | OH | H | OH | H | H | Ph(4 OH) | double bond |
| 20 | —O— | H | COOH | H | H | H | H | single bond |
| 21 | —O— | H | COOH | H | H | H | $CH_3$ | single bond |
| 22 | —O— | H | CH=CH—COOH | H | H | H | $CH_3$ | single bond |
| 23 | —$CH_2$— | H | H | H | H | H | H | double bond |
| 24 | —$CH_2$— | H | $OCH_3$ | H | H | H | H | double bond |
| 25 | —$CH_2$— | H | H | $OCH_3$ | H | H | H | double bond |
| 26 | —$CH_2$— | H | $OCH_3$ | Br | H | H | H | double bond |
| 27 | —$CH_2$— | H | H | H | $OCH_3$ | H | H | double bond |
| 28 | —$CH_2$— | H | COOH | H | H | H | H | double bond |
| 29 | —$CH_2$— | H | $CONH_2$ | H | H | H | H | double bond |
| 30 | —$CH_2$— | H | COOEt | H | H | H | H | double bond |
| 31 | —$CH_2$— | H | $CH_2OH$ | H | H | H | H | double bond |
| 32 | —$CH_2$— | H | H | COOH | H | H | H | double bond |
| 33 | —$CH_2$— | COOH | H | H | H | H | H | double bond |
| 34 | —$CH_2$— | $CONH_2$ | H | H | H | H | H | double bond |
| 35 | —$CH_2$— | H | $OCH_2COOEt$ | H | H | H | H | double bond |

| Comp | Z | R1 | R2 | R3 | R4 | R5 | R6 | |
|---|---|---|---|---|---|---|---|---|
| 36 | —CH2— | H | CH3<br>\|<br>O—C—COOEt<br>\|<br>CH3 | H | H | H | H | double bond |
| 37 | —CH2— | H | OCH2COOH | H | H | H | H | double bond |
| 38 | —CH2— | H | CH3<br>\|<br>O—C—COOH<br>\|<br>CH3 | H | H | H | H | double bond |
| 39 | —CH2— | H | CH=CH—COOH | H | H | H | H | double bond |
| 40 | —CH2— | H | CH=CH—COOEt | H | H | H | H | double bond |
| 41 | —CH2— | H | OH | CH3CO | H | H | H | double bond |
| 42 | —CH2— | H | OH | COOH | H | H | H | double bond |
| 43 | —CH2— | H | t-Bu | OH | H | H | H | double bond |
| 44 | —CH2— | H | CH2COOH | H | H | H | H | double bond |
| 45 | —CH2— | H | H | H | COOH | H | H | double bond |
| 46 | —CH2— | H | COOH | H | H | H | H | single bond |
| 47 | —CH2— | H | H | COOH | H | H | H | single bond |
| 48 | —CH2— | H | CH=CH—COOH | H | H | H | H | single bond |
| 49 | direct linkage | H | COOH | H | H | H | H | double bond |
| 50 | direct linkage | H | CH=CH—COOH | H | H | H | H | double bond |

The abbreviations i-Pr, cy-Pr, t-Bu, Ph, Py and Et mean respectively isopropyl, cyclopropyl, tert-butyl, phenyl, pyridyl and ethyl.

Among the compounds of the invention, the most preferred are the following ones:

1,2-dihydro-3-(1-imidazolyl)-6-carboxynaphthalene, the $C_1$–$C_4$-alkyl esters and the pharmaceutically acceptable salts thereof;

1,2-dihydro-3-(1-imidazolyl)-6-(2-carboxyisopropoxy)-naphthalene, the $C_1$–$C_4$ alkyl esters and the pharmaceutically acceptable salts thereof;

1,2-dihydro-3-(1-imidazolyl)-6-carbamoylnaphthalene and the pharmaceutically acceptable salts thereof.

The compounds of the invention can be prepared by a process comprising:

(a) converting a compound of formula (II)

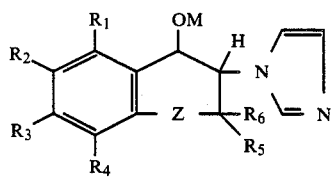

(II)

wherein $R_1$, $R_2$, $R_3$, $R_4$, $R_5$, $R_6$ and Z are as defined above and M represents hydrogen, or the residue of an active derivative of an acid, into a compound of formula (I), wherein $R_1$, $R_2$, $R_3$, $R_4$, $R_5$, $R_6$ and Z are as defined above and the symbol _____ represents a double bond; or (b) reducing a compound of formula (II), as defined above, thus obtaining a compound of formula (I), wherein $R_1$, $R_2$, $R_3$, $R_4$, $R_5$, $R_6$ and Z are as defined above and the symbol _____ represents a single bond; or (c) reducing a compound of formula (III)

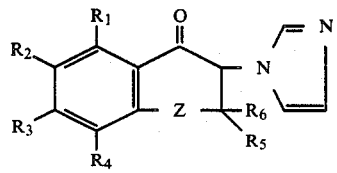

(III)

wherein $R_1$, $R_2$, $R_3$, $R_4$, $R_5$, $R_6$ and Z are as defined above, thus obtaining a compound of formula (I), wherein $R_1$, $R_2$, $R_3$, $R_4$, $R_5$, $R_6$ and Z are as defined above and the symbol _____ represents a single bond; or (d) reducing a compound of formula (IV)

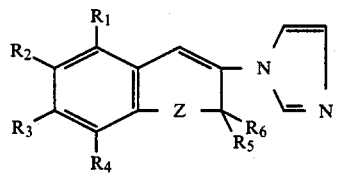

(IV)

wherein $R_1$, $R_2$, $R_3$, $R_4$, $R_5$, $R_6$ and Z are as defined above, thus obtaining a compound of formula (I), wherein $R_1$, $R_2$, $R_3$, $R_4$, $R_5$, $R_6$ and Z are as defined above and the symbol _____ represents a single bond; and, if desired, converting a compound of formula (I) into another compound of formula (I), and/or, if desired, converting a compound of formula (I) into a pharmaceutically acceptable salt thereof, and/or, if desired, converting a salt into a free compound, and/or, if desired, separating a mixture of isomers of formula (I) into the single isomers.

When M in a compound of formula (II) is the residue of an active derivative of an acid, that is an acyl group, it is, for example, a $C_2$-$C_4$ acyl, in particular acetyl, or it may be a mesyl or tosyl group.

The conversion of a compound of formula (II) into a compound of formula (I) according to process (a) reported above, may be carried out in the presence of a suitable solvent, such as, glacial acetic acid, mixtures of acetic anhydride-pyridine, dimethylformamide (DMF) or dimethylsulfoxide (DMSO), or benzene, in the presence of suitable amounts, even catalytic amounts, of a strong acid, e.g., concentrated $H_2SO_4$, HCl, or p-toluenesulphonic acid, at temperatures ranging from about 50° C. to the reflux temperature. The same conversion may also be performed by refluxing a compound of formula (II) in concentrated acids, e.g. hydrochloric or hydrobromic acid. When in a compound of formula (II) M is an acyl group, in particular, acetyl, the reaction may also be carried out by pyrolysis, at temperatures ranging, preferably, from about 200° C. to about 300° C. Reduction of compounds of formula (II), (III) and (IV) to obtain a compound of formula (I), according to processes (b), (c) and (d), may be performed, for example, by catalytic hydrogenation in the presence of suitable catalyst, e.g. palladium, platinum, $PtO_2$, ruthenium or Raney-nickel in a suitable solvent, preferably chosen from methyl alcohol, ethyl alcohol, acetic acid, cyclohexane, n-hexane, ethyl acetate, benzene or toluene, operating at a pressure ranging from atmospheric pressure to about 30 atmospheres and at temperatures ranging from room temperature to about 100° C. In particular, a compound of formula (II), wherein M represents tosyl or mesyl, may be reduced with $Li(C_2H_5)_3BH$ in an anhydrous aprotic solvent, preferably chosen from diethylether and tetrahydrofurane (THF). A compound of formula (III) may also be reduced according to the Clemmensen procedure, i.e. with zinc amalgam in hydrochloric acid.

A compound of formula (I) may be converted, if desired, into another compound of formula (I).

These optional conversions may be carried out by methods known in themselves.

Thus, for example, a compound of formula (I) wherein one or more of $R_1$, $R_2$, $R_3$ and $R_4$ is hydrogen may be converted into a compound of formula (I) wherein one or more of $R_1$, $R_2$, $R_3$ and $R_4$ is a halogen atom, e.g. chlorine or bromine, by reaction with chlorine or bromine in the presence of a Friedel-Crafts catalyst, preferably $AlCl_3$, operating in a suitable solvent, e.g. $CH_2Cl_2$.

A compound of formula (I), wherein one or more of $R_1$, $R_2$, $R_3$ and $R_4$ is hydrogen may be converted into a compound of formula (I), where one or more of $R_1$, $R_2$, $R_3$ and $R_4$ is $C_1$-$C_6$ alkyl, by alkylation through a Friedel-Crafts reaction, e.g. by reaction with (a) a $C_1$-$C_6$ alkylhalide, preferably chloride, bromide or iodide; or with (b) a $C_1$-$C_6$ alcohol in a suitable solvent, e.g. nitrobenzene or $CH_2Cl_2$, or $CS_2$.

In both the cases (a) and (b), the reaction is performed in the presence of appropriate amounts of a Friedel-Crafts catalyst, such as $AlCl_3$, $ZnCl_2$, or $BF_3$; and when a $C_1$-$C_6$-aliphatic alcohol is used, also in the presence of a strong mineral acid such as HF, $HClO_4$ or, if desired, in concentratedd $H_2SO_4$ or in concentrated $H_3PO_4$ without additional solvent, at temperatures ranging from the room temperature to 100° C.

A compound of formula (I) wherein one or more of $R_1$, $R_2$, $R_3$ and $R_4$ is a $C_1$-$C_6$ alkoxy group may be converted into a compound of formula (I) wherein one or more of $R_1$, $R_2$, $R_3$ and $R_4$ is hydroxy group by following conventional procedures well known in organic chemistry. For example by treatment with a strong mineral acid, i.e. HCl, HBr, HI, preferably HBr, at temperature ranging from 30° C. to the reflux temperature, preferably at reflux temperature, or by treatment with a Lewis acid, for example $AlCl_3$ or $BF_3$, in a suitable solvent, i.e. $CH_2Cl_2$ or nitrobenzene, at temperatures ranging from the room temperature to 80° C. A compound of formula (I) containing an esterified carboxy group, may be converted into a compound of formula (I) containing a free carboxy group, by acidic or alcaline hydrolysis, operating at temperature ranging from the room temperature to about 100° C.

A compound of formula (I) containing a free carboxy group, may be converted into a compound of formula (I) containing an esterified carboxy group by esterification, e.g. via the corresponding acid halide, e.g. chloride reacting with an excess of a suitable $C_1$-$C_6$ alkyl alcohol, or by direct esterification by means of acidic catalysis i.e. in the presence of dry HCl or $SOCl_2$ or $BR_3$-etherate. A compound of formula (I) containing a carbamoyl group may be converted into a compound of formula (I) containing a free carboxy group by hydrolysis, preferably by acid hydrolysis, in a suitable solvent, such as water, or by the Bouveault procedure, that is by treatment with $NaNO_2$ and an aqueous strong inorganic acid, i.e. $H_2SO_4$, operating at temperatures ranging between the room temperature and 100° C.

A compound of formula (I) containing a free or esterified carboxy group may be converted in a compound of formula (I) containing a

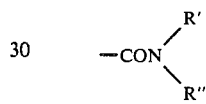

group, wherein R' and R'' are as defined above.

Accordingly, the conversion of an esterified carboxy group into the corresponding amide may be performed by direct reaction with ammonia or an appropriate amine in a suitable solvent, e.g., ether or benzene or using an excess of the amine as solvent, at temperatures ranging from room temperature to reflux.

The conversion of free carboxy group into the corresponding amides may be carried out via an intermediate reactive derivative which may be isolated or not.

Intermediate reactive derivatives may be active esters e.g. $NO_2$-phenyl esters, or N-hydroxysuccinimide esters, acid halides, preferably chloride, mixed anhydrides e.g. ethoxycarbonyl or tert-butylcarbonyl anhydrides, or the reactive intermediates obtained in situ by reaction of the acid with dicyclohexylcarbodiimide or carbonyldiimidazole.

The reactive intermediates obtained following conventional ways, as those usually employed in the synthesis of peptides, are reacted with ammonia or an appropriate amine in a suitable solvent or with an excess of the amine itself at temperatures ranging from about −10° C. to about 50° C.

A compound of formula (I) wherein one of $R_1$, $R_2$, $R_3$ and $R_4$ is a free or esterified carboxy group, in particular a lower alkoxycarboxyl group, may be converted into a compound of formula (I) wherein one or $R_1$, $R_2$, $R_3$ and $R_4$ is a $CH_2OH$ group by reduction in conventional ways, preferably with $LiAlH_4$ in a suitable solvent, e.g. ethylether or THF.

A compound of formula (I) wherein one of $R_1$, $R_2$, $R_3$ and $R_4$ is a free or esterified carboxy group, in particular a lower alkoxycarbonyl group, may be converted into a compound of formula (I) wherein one of $R_1$, $R_2$, $R_3$ and $R_4$ is, for example, a

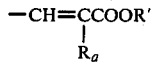

group, wherein $R_a$ and $R'$ are as defined above, by reducing first the free or esterified carboxy group to a formyl group, then condensing the obtained aldehyde with the desired phosphorane-acetate or phosphonate-acetate following a Witting or Horner-Emmons procedure, or in addition, in the case that the desired $R_a$ is hydrogen, condensing the above aldehyde with diethylmalonate, following a malonic synthesis procedure, heating then the obtained malonate with strong mineral acids to hydrolyze and decarboxylate it.

The above mentioned reduction to aldehyde may be performed:

(a) starting from an esterified carboxy group by using diisobutylaluminium hydride (DIBAH), or with diaminoaluminium hydrides;

(b) starting from a free carboxy group by using bis-(4-methylpiperazinyl)aluminium hydride in THF, or diisobutylaluminium hydride, or diaminoaluminium hydrides;

(c) starting from a free carboxy group previously transformed in the acid chloride in conventional ways e.g. by $SOCl_2$, by reducing the chloride with Lithium-tri-t-butoxy-aluminium hydride or by a conventional Rosenmund hydrogenation procedure using poisoned platinum catalyst, or by using tri-butyltin hydride.

The above mentioned Wittig condensation can be carried out e.g. with

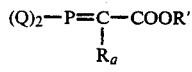

wherein Q is phenyl or lower alkyl, $R_a$ is as above defined and $R'$, being as defined above, is, preferably, methyl or ethyl, in a suitable solvent, preferably, in dimethoxyethane or THF or DMSO at temperatures ranging from room temperature to about 60° C. The analogues Horner-Wittig procedure may be carried out, e.g., with

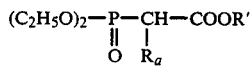

wherein $R_a$ is as above defined and $R'$ is, preferably, methyl or ethyl in the same solvent mentioned above for the Wittig procedure in the presence of a strong base, such as, sodium hydride, butyl lithium, or sodium amide.

The above described malonic synthesis may be performed using as condensing agent an alkali metal alkoxide, e.g. potassium tert-butoxide in tert-butanol, and the subsequent hydrolysis and decarboxylation may be performed by boiling in a suitable acid, e.g. conc. HCl.

A compound of formula (I) wherein one of $R_1$, $R_2$, $R_3$ and $R_4$ is a free or esterified carboxy group or a carbamoyl group may be converted into a compound of formula (I) wherein one of $R_1$, $R_2$, $R_3$ and $R_4$ is a 5-tetrazolyl group by transforming, first, the carboxy or carbamoyl group into a CN group, and then reacting the obtained nitrile with $NaN_3$ in DMF or a mixture CH$_3$COOH/tert-BuOH, thus getting a 5-tetrazolyl derivative of formula (I).

The above mentioned nitrile may be obtained, e.g.:

(a') directly from the free carboxy group, by reaction with chlorosulfonylisocyanate and subsequent decomposition by heating in DMF the corresponding chlorosulfonylamide;

(b') directly from the carbamoyl group by dehydration with chlorosulfonylisocyanate or $POCl_3$ or dicyclohexylcarbodiimide (DCC); or (c') from free or esterified carboxy group, previously transformed in a formyl group, by one of the reductive methods above mentioned.

The obtained aldehyde is then transformed in the corresponding oxime, which isolated or not is transformed into nitrile by dehydrating agents e.g. as DCC.

A compound of formula (I) wherein one of $R_1$, $R_2$, $R_3$ and $R_4$ is an —OH or —SH group may be converted into a compound of formula (I) wherein one of $R_1$, $R_2$, $R_3$ and $R_4$ is

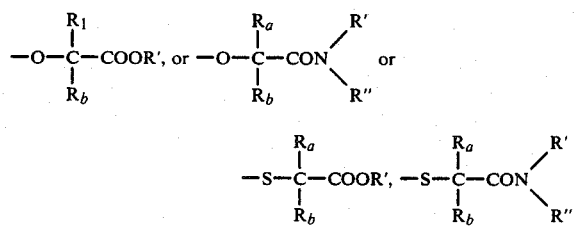

wherein $R_a$, $R_b$, $R'$ and $R''$ are as above defined, by reaction with compounds of formula

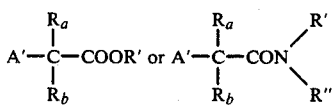

wherein $A'$ is a halogen atom, preferably chlorine or bromine or an active ester group, preferably a tosylate group, in the presence of a suitable base in a suitable solvent e.g. with tert-BuOK in tert-BuOH, or with anhydrous $K_2CO_3$ in acetone or with sodium hydride in DMF at temperatures ranging from room temperature to reflux.

The optional salification of a compound of formula (I) as well as the conversion of a salt into the free compound and the separation of a mixture of isomers into the single isomers may be carried out by conventional methods.

For example the separation of a mixture of geometric isomers, e.g. cis- and trans-isomers, may be carried out by fractional crystallization from a suitable solvent or by chromatography, either column chromatography or high pressure liquid chromatography.

A compound of formula (II), wherein M represents hydrogen may be obtained by reducing a compound of formula (III), according to well known procedures, for example, by treatment with an alkali metal borohydride, e.g. $NaBH_4$, in a suitable solvent, e.g. methyl or ethyl alcohol or a mixture of water and ethyl alcohol, or by treatment with $LiAlH_4$ in an anhydrous solvent, e.g. diethyl ether or tetrahydrofuran, at a temperature ranging, in both cases, preferably between 0° C. and the reflux temperature, for reaction times varying approximately from 1 to 6 hours.

A compound of formula (II), wherein M represents the residue of an active derivative of an acid, as defined above, may be obtained according to known methods, e.g. by reacting a compound of formula (II) wherein M is hydrogen, with the suitable acyl or sulfonyl halide, preferably chloride, for example, with acetylchloride or with tosyl or mesyl chloride operating e.g. in anhydrous pyridine or in an inert solvent, e.g. anhydrous benzene, if desired in the presence of an equimolar amount of a base such as triethylamine, at temperatures ranging from room temperature to about 60° C.

The compounds of formula (III) may be prepared, for example, by a process comprising:
(a) reacting a compound of formula (V) or a derivative thereof

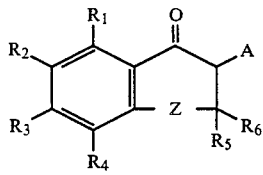

wherein $R_1$, $R_2$, $R_3$, $R_4$, $R_5$, $R_6$ and Z are as above defined and A is halogen or an active ester group, with imidazole or a salt thereof; or, when in a compound of formula (II) Z is oxygen, also
(b) reacting a compound of formula (VI)

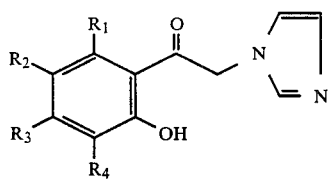

wherein $R_1$, $R_2$, $R_3$ and $R_4$ are as above defined with a compound of formula (VII)

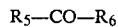     (VII)

wherein $R_5$ and $R_6$ are as defined above, or with a reactive compound thereof.

A derivative of a compound of formula (V) may be a compound in which the carbonyl group is protected before the reaction with imidazole or a salt thereof takes place, and then removed, at the end of the reaction, by following known methods.

The carbonyl group may be protected for example in the form of a ketale group of formula

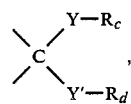

in which Y and Y', independently, are oxygen or sulphur and each of $R_c$ and $R_d$, whether the same or different, is $C_1$-$C_6$ alkyl or $R_c$ and $R_d$, taken together, form a straight or branched $C_2$-$C_6$ alkylene chain.

The carbonyl group is preferably protected in the form of a 1,3-dioxolan group.

When in a compound of formula (V) A is a halogen atom, it is preferably chlorine or bromine and when it is an active ester group, it is preferably —O-tosyl or —O-mesyl.

A salt of imidazole is preferably an alkali metal, e.g. sodium or potassium salt or a silver salt. The reaction of a compound of formula (V) or a derivative thereof with imidazole or a salt thereof is preferably carried out either
(a) in the absence of solvent, at a temperature preferably ranging between the room temperature and about 180° C. and for reaction times which may vary from some minutes to about 20 hours using, if necessary, an excess of imidazole or a salt thereof, or
(b) in the presence of a suitable solvent, preferably dimethylformamide, dimethylacetamide, hexamethylphosphorotriamide, benzene, toluene, ethyl acetate, ethyl alcohol, dioxane or acetone, at a temperature preferably ranging between about 0° C. and the reflux temperature, for reaction times varying from some minutes to about 12 hours and using, if necessary, an excess of imidazole or a stoichiometric amount of a tertiary base, preferably triethylamine.

The protection of a compound of formula (V) in the form of a 1,3-dioxolan group may be performed by following well known procedures, e.g. by reacting a compound of formula (V) with diethyleneglycol in the presence of strong inorganic or organic acids, i.e. p-toluenesulphonic acid, to give the corresponding 1,3-dioxolan, i.e. 1,2-ethylenedioxy, derivative. As stated above the protecting group, after reaction with imidazole, is removed by following usual procedures, e.g. by treatment with diluted aqueous inorganic acids.

The reaction of a compound of formula (VI) with a compound of formula (VII) or a reactive derivative thereof, which may be, for instance, a bisulphite addition compound, may be performed by using a suitable solvent, e.g. water, methyl or ethyl alcohol or acetic acid, or mixtures of these solvents with water or if desired using as solvent an excess of compound (VII), at a temperature preferably ranging between about the room temperature and the reflux temperature for reaction times varying from few minutes to some hours. In the case that the compound of formula (VII) is formaldehyde, $R_5$ and $R_6$ being hydrogen, a reactive derivative thereof may be paraformaldehyde or trioxymethylene.

The compounds of formula (IV) are compounds covered by the general formula (I), wherein the symbol represents a double bond, and may be obtained, for example, according to process (a), described above.

A compound of formula (V) in which A is a halogen atom may be obtained by halogenating the corresponding compound of formula (VIII)

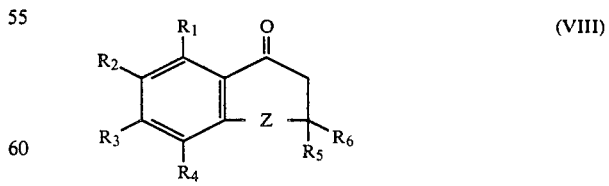

wherein $R_1$, $R_2$, $R_3$, $R_4$, $R_5$, $R_6$ and Z are as defined above.

The halogenation of a compound of formula (VIII) to give a compound of formula (V) may be carried out:
(a) with a stoichiometric amount of halogen, preferably bromine or chlorine, in a suitable solvent, e.g. diethyl ether, methylene chloride, CHCl₃, CCl₄, CS₂ or acetic acid, at a temperature ranging from about 0° C. to about 100° C.;

(b) by reaction with the stoichiometric amount of CuBr₂ in a suitable solvent e.g. ethyl acetate, at temperatures ranging from about 50° C. to the reflux temperature;

(c) by using a stoichiometric amount of sulphuryl chloride in a suitable solvent, e.g. methylene chloride, chloroform or benzene at temperatures ranging from the room to the reflux temperature.

In all the above cases (a), (b) and (c), the reaction times may range between 3 and 12 hours.

A compound of formula (V) wherein A is -O-tosyl or -O-mesyl may be obtained by reacting the corresponding alcohol, that is practically a compound of formula (V) wherein, but only in this compound, A is hydroxyl [which is known or may be prepared by known methods], with p-toluenesulphonyl or methanesulphonyl halide, preferably the chloride.

The reaction is preferably carried out in an anhydrous inert solvent, e.g. acetone, at temperature ranging from the room to the reflux temperature.

A compound of formula (VI) may be obtained by reacting a compound of formula (IX)

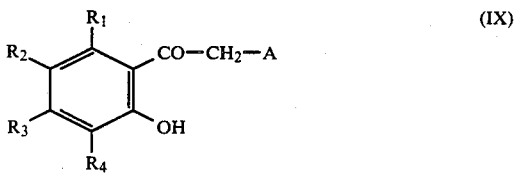

wherein $R_1$, $R_2$, $R_3$, $R_4$ and A are as defined above, with imidazole or a salt thereof, preferably an alkali metal, e.g. sodium or potassium salt, or a silver salt.

The reaction may be carried out using the same reaction conditions reported above for the reaction between a compound of formula (V) and imidazole or a salt thereof. The compounds of formula (VII) are known compounds. Also the compounds of formula (VIII) are known or they may be prepared by known methods from known compounds. For instance, a compound of formula (VIII) in which $R_1$, $R_2$, $R_3$, $R_4$, $R_5$, $R_6$ and Z are as above defined, may be obtained by cyclizing a compound of formula (X)

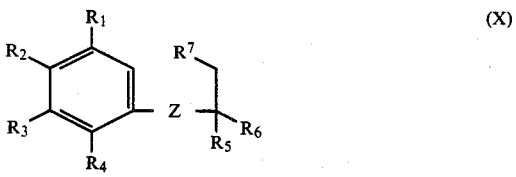

wherein $R_1$, $R_2$, $R_3$, $R_4$, $R_5$, $R_6$ and Z are as above defined and $R_7$ is cyano, carboxy, ($C_1$–$C_7$ alkoxy)carbonyl or the group —$COR_8$, wherein $R_8$ is a halogen atom.

The cyclization of a compound of formula (X) in which $R_7$ is cyano, carboxy or ($C_1$–$C_7$ alkoxy)carbonyl, may be carried out by treatment with a suitable cyclizing agent, e.g. phosphoric anhydride, polyphosphoric acid, chlorosulphonic acid or sulphuric acid, optionally in the presence of a suitable solvent, preferably chosen from benzene, toluene and xylene, at a temperature which may range from about 20° C. to about 130° C. The cyclization of a compound with formula (X) wherein $R_7$ is the group —$COR_8$ and $R_8$ is as defined above, is preferably carried out by using AlCl₃ in the presence of a suitable solvent, e.g. carbon disulphide, at temperatures ranging from about 0° C. to about 50° C.

The compounds of formula (IX) and (X) are known or may be prepared by known methods starting from known compounds. When in the compounds having the formulae (I), (II), (III), (IV), (V), (VI), (VII), (VIII), (IX) and (X) groups are present which need to be protected during the reactions reported above, e.g. amino, hydroxy, further carboxy groups, etc., such groups can be protected in a conventional way before the reaction takes place.

Examples of protecting groups are those usually employed in the synthesis of peptides, for example, to protect amino groups, acetyl, benzoyl, tert-butoxy-carbonyl, p-methoxy-benzyloxy-carbonyl, o-nitro-phenyl-sulphonyl, dichloroacetyl protective groups may be employed.

To protect hydroxy groups acetyl, benzoyl, benzyloxy, tetrahydropyranyl, β-methoxyethoxymethyl (MEM) or a trialkylsilyl as tert-butyldimethylsilyl groups may be, for instance, employed. To protect the carboxy groups, tert-butyl, benzhydryl and p-methoxybenzyl groups may be employed.

The protecting groups are then removed, at the end of the reaction, in a known manner, e.g. by mild acid hydrolysis or by mild catalytic reduction, for example with Pd/C as catalyst at atmospheric pressure.

The amino, carboxy and hydroxy protecting groups are then removed at the end of the reaction, usually in a known manner. For example, when the amino protecting group is the monochloroacetyl group, it may be removed by treatment with thiourea; the formyl and the trifluoroacetyl groups may be removed by treatment with potassium carbonate in aqueous methanol and the trityl group by treatment with formic or trifluoroacetic acid.

The carboxy protecting groups, for example, may be removed by mild acid hydrolysis or by catalytic hydrogenation, e.g. with Pd/C at room pressure.

The hydroxy protecting groups, for instance, may be removed by mild reaction conditions, e.g. acid hydrolysis.

The compounds of this invention are selective inhibitors of Thromboxane A₂ (TxA₂) synthesis and stimulators of Prostacyclin (PGI₂) synthesis.

The activity on TxA₂ and PGI₂ synthetase has been evaluated in vivo. For example, rats were treated with a single oral dose of compound and killed 2 hours later.

TxB₂ and 6-keto-PGF$_{1\alpha}$ concentrations, the stable metabolites of TxA₂ and PGI₂ respectively, were determined on serum and plasma respectively.

For example, the compound 1,2-dihydro-3-(1-imidazolyl)-6-carboxy-naphthalene (internal code compound FCE 22178) dosed up to 9 mg/kg reduced serum TxB₂ concentration up to 70% and increased plasma 6-keto-PGF$_{1\alpha}$ concentration up to 30%. The same compound dosed at 100 mg/kg reduced serum TxB₂ concentration by 90% and doubled plasma 6-keto-PGF$_{1\alpha}$ concentration.

In most tissues the main products of arachidonic acid metabolism are PGI₂ and TxA₂ and their ratio plays a paramount role is vascular haemostasis. PGI₂ has antiaggregatory and vasodilatory activity while TxA₂ is a proaggregatory (or aggregatory) and vasoconstrictor compound. The enzyme PGI₂ synthetase is located mainly in the endothelial cell and produces PGI$_2$ which avoids adhesion of platelets to the arterial wall and production of thrombi and has a vasodilatory activity.

The enzyme TxA$_2$ synthetase in turn is mainly located in platelets and produces TxA$_2$ which blocks haemorrhage via the formation of platelet aggregates and vasoconstriction. Balancing the opposite activities, vascular haeomostasis is regulated.

The compounds of the invention, being able to inhibit selectively the formation of TxA$_2$, can be used as vasodilatory and antiaggregant agents, for example in all the cases of thrombosis, periferal vasculopaties and coronary artery disease. In fact inhibition of TxA$_2$ production reduces the probability of thrombi formation and of vasoconstriction with consequent ischemic events and, leaving unaltered (or increasing) PGI$_2$ production, improves vasodilation, tissue blood supplies and protects the vessel wall.

Another use of the compounds of the invention is for the treatment of migraine. As is known, for example, in the case of migraine it has been demonstrated a diffused vasoconstriction induced by platelet TxA$_2$ overproduction [J. Clin. Pathol. (1971) 24, 250; J. Headache (1977) 17, 101].

A platelet overproduction of TxA$_2$ and MDA (malondialdehyde) in diabetes mellitus has been demonstrated and correlated with microcirculatory defects in the illness [Metabolism (1979) 28, 394; Eu. J. Clin. Invest. (1979) 9, 223; Thrombosis Haemost. (1979), 42, 983; J. Lab. Clin. Med. (1981) 97, 87].

Therefore, the compounds of the invention can be used, e.g., in the treatment of diabetic microangiopathy.

Moreover, the compounds of the invention can be used as anti-inflammatory agents. As is known, for example, fluid obtained from carrageenin-induced granuloma converts arachidonic acid into TxA$_2$ in vitro and TxA$_2$ levels are increased in the synovial fluid of rheumatoid arthritis patients and in the fluid of carrageenin-induced inflammation in rats [Prostaglandins (1977) 13, 17; Scand. J. Rheum. (1977) 6, 151]. Recently it has been also demonstrated that an overproduction of TxA$_2$ is involved in the pathogenesis of hypertension and that a specific inhibitor of TxA$_2$ production may be employed in the elimination of such a factor in hypertension [Eu. J. Pharmacol. (1981) 70, 247].

In fact the compounds of the invention can be used as hypotensive agents.

For example, one of the compound of this invention, i.e. compound FCE 22178, was given orally to nine male SHR rats for seven weeks at the dosage of 9 mg/kg.

The mean systemic pressure was monitored on an eight channels Beckman polygraph via a Statham pressure transducer, connected to a PE 60 catheter, inserted, 24 hours before monitoring, into the left carotid artery. The compound decreased the development of hypertension in this model, as shown by Table 1.

TABLE 1

| Treatment (weeks) | Mean systemic pressure | |
|---|---|---|
| | Controls mm Hg ± E.S. | Treated mm Hg ± E.S. |
| 7 | 177 ± 5.06 | 154.8 ± 14.1 |

Furthermore it has been shown a role of TxA$_2$ in the pathogenesis of ulcerative disorders of the stomach in accordance with its powerful gastric vasoconstrictory activity, so that also in this field a TxA$_2$ inhibitor is useful [Nature (1981) 292, 472]. In fact the compounds of the invention are indicated for the treatment of peptic ulcers. The compounds of the invention can be also antitumoral agents. It is known, for example, that a selective inhibition of TxA$_2$ synthesis has been demonstrated to reduce the number of lung methastases and to slow down tumor growth [Nature (1982) 295, 188].

In view of the correlation between TxA$_2$ synthesis and calcium transport, recently showed by some authors, specific TxA$_2$ synthetase inhibitors, such as the compounds of the invention, can also find use in the treatment of osteoporosis, e.g. postmenopausal osteoporosis [Prostaglandins (1981) 21, 401].

Moreover the compounds of the invention are indicated for the treatment of angina pectoris.

In this respect, it is known, for example, that high levels of TxB$_2$ have been found in patients with Prinzmetal's angina [Prostaglandins and Med. (1979) 2, 243] and in patients with recurrent angina attacks [Sixth Intern. Congress on Thrombosis, Monte Carlo October 1980 Abs n°. 140].

The platelet antiaggregatory activity of the compounds of the invention was evaluated in vitro and in vivo, for example, according to the modified methods of Born [Born G.V.R., Nature 194, 927 (1962)] and Silver [Silver M. J., Science 183, 1085 (1974)].

The compounds of this invention were found in vitro to have inhibitory activity on platelet aggregation induced by collagen or ADP (adenosine-5'-disphosphate) in platelet rich plasma of guinea pig [Dunkin Hantley Iva: PDH (SPF) Ivanovas GmBH, Germany]. For example the compound 1,2-dihydro-3-(1-imidazolyl)-6-methoxy-naphthalene (internal code compound FCE 22466) was found to be active both on ADP and on collagen-induced platelet aggregation: at 25 mcg/ml it totally inhibits collagen-induced platelet aggregation in three out of four samples of platelet rich plasma.

The compounds of this invention are more potent as inhibitors of the platelet aggregation, induced in vitro, e.g., by collagen, than the compounds previously disclosed in U.S. Pat. No. 4,342,775 and in U.K. published Patent Application 2,106,509 A.

The results obtained, for example, by testing the compound of the invention FCE 22466 and the known ones 3-(1-imidazolyl)-2,3-dihydro-6-chloro-4H-1-benzopyran-4-one (internal code compound FCE 20204), which is described in U.S. Pat. No. 4,342,775, and 2-(1-imidazolyl)-3,4-dihydro-7-methoxy-1(2H)-naphthalenone (internal code compound FCE 21848), which is described in U.K. published Patent Application 2,106,509 A, are shown by Table 2.

TABLE 2

| Compound | In vitro concentration mcg/ml | % Inhibition |
|---|---|---|
| FCE 22466 | 12.33 | 50 |
| FCE 20204 | 12.50 | 0 |
| FCE 21848 | 12.50 | 0 |

The compound FCE 22178 was also suspended in Methocel ® and administered orally by gavage to rabbits (New Zealand White) at 2 mg/kg one hour before the injection of 1.4 mg/kg of arachidonic acid.

The test compound greatly decreases the arachidonic acid induced mortality (Table 3):

TABLE 3

Effect of the compound FCE 22178 on the arachidonic acid (1.4 mg/kg) induced mortality in rabbits.

| Treatment | dose mg/kg/os | Mortality |
|---|---|---|
| Methocel$^R$ | — | 9/9 |
| Compound FCE 22178 | 2 | 3/9 |

As stated above, certain compounds of the present invention, and exactly those wherein one of $R_1$, $R_2$, $R_3$ and $R_4$ is a group

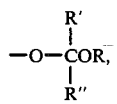

and the others are defined as in formula (I), have no activity on the $TxA_2/PGI_2$ system, but are surprisingly endowed with a very high activity in lowering cholesterol and triglycerides, in increasing the total serum HDL cholesterol, as well as in increasing the ratio between α-lipoprotein and β-lipoprotein total cholesterol. As is known, drugs having such activities are useful in prevention and therapy of atherosclerosis: Glueck C.J., Artery, 2, 196 (1976); Day C. E. in Frank-H-Clarke (Ed.) Annual reports in Medicinal Chemistry, 13, 184, chapter 2—Academic Press, N.Y. 1978.

The substituent

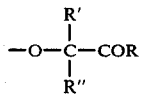

is missing in the compounds of the above mentioned U.S. Pat. No. 4,342,775 and U.K. published Patent Application 2,106,509 A, but such known compounds are nevertheless endowed with lipid lowering and anti-atherosclerotic activity.

The introduction of this new substituent in the new bicyclic compounds has therefore unexpectedly strengthened these activities. The activity of this particular group of compounds of this invention and of the compounds of the above mentioned U.S. Patent and U.K. published Patent Application was evaluated on groups of Icem: CER (SPF Caw) male rats either fed for six days with hypercholesterolaemic diet according to C. E. Day [Schurr P. E., Schultz H. R., Day C. E. (Eds) Atherosclerosis and drug discovery—Plenum Pub. Corp., 217 (1976)] (Experiment No. 1) or fed standard diet [Altromin](Experiment No. 2). "Altromin" is a trade mark. The compounds were suspended in "Methocel" (methyl cellulose, a 0.5% suspension in water) and administered by stomach tube for 4 days.

Groups of animals were treated with the suspending agent only (control groups).

The total serum cholesterol was determined with the method of Trinder P. J. [J. Clin. Pathol., 22, 246 (1969)].

The serum triglycerides were determined with the method of Mendez J. [J. Clin. Chem., 21, 768, (1975)].

The total serum HDL cholesterol was determined according to Demacker P. N. M. [Clin. Chem., 23, 1238, (1977)]. Statistical analysis in experiment No. 1 was performed by the Student's t test for independent samples or by the Cochran's test when the variances were not homogeneous at the F ratio test [Bliss C. I.—Statistics in Biology, Vol. 1, page 213—McGraw Hill Book Company, New York, 1967; Cochran W. G., Cox G. M.—Experimental designs—J. Wiley & Sons Inc., New York, II Ed. (1968) page 100]. For the experiment No. 2 the following statistical methods were applied: the variance analysis, Bartlett test [Properties of sufficiency and Statistical Tests—Proc. of the Royal Soc. of London A 160 (1937) pages 268–282] to prove the variance homogeneity and the Dunnett test [Dunnett C. W.—J. Amer. Stat. Ass., 50, 1096 (1955)]. In the animal treated with hypercholesterolaemic diet the tested compounds of this invention were found to decrease the total serum cholesterol and to increase the total serum HDL cholesterol in a highly significant way, while at similar dosage levels the compounds of the prior art were weakly active.

Table 4 exemplifies the results obtained, e.g., by testing the compound of this invention 1,2-dihydro-3-(1-imidazolyl)-6-(2-carboxy-isopropoxy)-naphthalene (internal code FCE 22473) and the known one FCE 20204

TABLE 4

| | (Experiment No. 1) | |
|---|---|---|
| Treatment | Dosage mg/kg/os | Total serum cholesterol % variation vs. controls | Serum HDL cholesterol % variation vs. controls |
| FC 22473 | 27 | −73 | +77 |
| FC 20204 | 25 | +7 | +49 |

In the animal fed standard "Altromin" diet the tested compounds of this invention were found to decrease both the total serum cholesterol and serum triglycerides, while the compounds of the prior art were found to be less active and to have similar activity only when administered at higher doses. Table 5 exemplifies the results obtained, e. g., by testing the compound of this invention FCE 22473 and the known one FCE 21848.

TABLE 5

| | (Experiment No. 2) | |
|---|---|---|
| Treatment | Dosage mg/kg/os | Total serum cholesterol % variation vs. controls | Serum triglycerides % variation vs. controls |
| FCE 22473 | 16.67 | −32 | −57 |
| FCE 21848 | 50.00 | inactive | inactive |

In view of their elevated lipid lowering activity and of their action on HDL cholesterol the compounds of this invention, wherein one of $R_1$, $R_2$, $R_3$ and $R_4$ is a radical

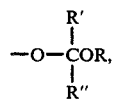

and the other substituents are defined as in formula (I), can therefore be used in therapy for treating dislipidaemies and atherosclerosis.

The dosage level suitable for oral administration to adult humans of the compounds of the invention, e.g. 1,2-dihydro-3-(1-imidazolyl)-6-carboxy-naphthalene, may range from about 5 mg to about 500 mg per dose 1 to 3 times a day, preferably from about 20 mg to about 150 mg per dose 1 to 3 times a day depending on the disease, age and weight of the patients involved.

The toxicity of the compounds of the invention is negligible, therefore they can be safely used in therapy. Nine hours food deprived mice and rats were treated orally with single administration of increasing doses, then housed and normally fed. The orientative acute toxicity ($LD_{50}$) was assessed on the seventh day after the treatment and resulted higher than 3000 mg/kg.

On the contrary, the $LD_{50}$ value of some known compounds having similar chemical structure, for example that of the compounds 1,2-dihydro-3-(1-imidazolylmethyl)-naphthalene and 1,2-dihydro-3-(1-imidazolylmethyl)-7-methoxy-naphthalene, described in published Japanese Patent Application No. 158435/1979 (L.O.P. No. 81566/1981) as very active in inhibiting $TxA_2$ synthetase, was found to be lower than 200 mg/kg/os, when assessed in the mouse according to the same procedure.

The compounds of the invention can be administered in a variety of dosage forms, e.g., orally, in the form of tablets, capsules, sugar, or film coated tablets, liquid solutions or suspensions, rectally, in the form of suppositories, parenterally, e.g. intramuscularly, or by intravenous injection or infusion.

In emergency situations the preferred one is intravenous. The exact dosage depends on the disease, age, weight, conditions of the patient and administration route.

The invention includes pharmaceutical compositions comprising a compound of the invention in association with a pharmaceutically acceptable excipient (which can be a carrier or diluent).

The pharmaceutical compositions containing the compounds of the invention are usually prepared following conventional methods and are administered in a pharmaceutically suitable form.

For example, the solid oral forms may contains, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and; in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions, and suspensions. The syrups may contains as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g. sterile water, olive oil, ethyl oleate, glycols, e.g., propylene glycol, and if desired, a suitable amount of lidocaine hydrochloride.

The solutions for intravenous injections or infusions may contain as carrier, for example, sterile water or preferably they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The I.R. spectrum of the compounds was measured in solid phase (KBr) or Nujol solution or in a solution of a suitable solvent such as $CHCl_3$, using Perkin-Elmer 125 spectrophotometer.

The N.M.R. spectrum was measured preferably in solution of dimethyl sulphoxide-$d_6$ or of $CDCl_3$, using a 90 M-hertz Bruker HFX apparatus.

The $R_f$ values were determined by thin layer chromatography on ready-to-use silica gel plates of 0.25 mm coating thickness.

The following examples illustrate but do not limit the invention.

EXAMPLE 1

A solution of 3-(1-imidazolyl)-2,3-dihydro-6-chloro-4H-1-benzopyran-4-ol (5.4 g), acetic acid (81 ml) and sulphuric acid (27 ml) was heated at 80° C. for 8 hours. The solution, poured into ice water (200 ml), neutralized with $NH_4OH$, extracted with $CH_2Cl_2$, dried and evaporated to dryness gave 3.9 g of 3-(1-imidazolyl)-6-chloro-2H-1-benzopyran, m.p. 118°-120° C. (isopropyl alcohol).

Analysis of the elements: Found: C 61.61; H 3.93; N 11.89; Cl 15.35. Calculated for $C_{12}H_9ClN_2O$: C 61.94; H 3.90; N 12.04; Cl 15.24.

T.L.C.: eluant $CH_2Cl_2:CH_3OH$ (170:30).

Rf 0.66.

N.M.R. ($CDCl_3$) $\delta$p.p.m.: 5.11 (2H, d, —O—$CH_2$), 6.49 (1H, br s, —O—$CH_2$—C=$CH$—), 6.84-7.78 (6H, m, aromatics+imidazole).

Analogously, the following compounds were prepared: 2-methyl-3-(1-imidazolyl)-6-carboxy-2H-1-benzopyran, m.p. 216°-220° C. and 225°-227° C. (according to crystallization form).

Analysis of the elements: Found: C 65.20; H 4.75; N 10.54. Theoretical for $C_{14}H_{12}N_2O_3$: C 65.61; H 4.72; N 10.93.

N.M.R. (DMSO-$d_6$) $\delta$p.p.m.: 1.36 (3H, d, —$CH_3$—), 5.76 (1H, q, —O—$CH$—), 6.99 (1H, s, —O—$CH$=C=$CH$—), 8.29 (1H, br s, —N—$CH$=N—), I.R. (KBr): $\nu$(O—H) carboxylic acid 3000-2300 $cm^{-1}$. $\nu$(C=O) carboxylic acid 1680 $cm^{-1}$.

3-(1-imidazolyl)-6-methoxy-2H-1-benzopyran, m.p. 104°-106° C.

Analysis of the elements: Found: C 68.20; H 5.33; N 12.24. Calculated for $C_{13}H_{12}N_2O_2$: C 68.40; H 5.30; N 12.27. T.L.C.: eluant $CH_2Cl_2:CH_3OH$ (180:20).

Rf=0.4.

N.M.R. ($CDCl_3$) $\delta$p.p.m.: 3.77 (3H, s, —O—$CH_3$), 5.00 (2H, d, —O—$CH_2$—), 6.46 (1H, br s,

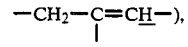

6.61-7.74 (6H, m, aromatics+imidazole).

3-(1-imidazolyl)-6-carboxy-2H-1-benzopyran, m.p. >290° C.

Analysis of the elements: Found: C 64.1; H 4.12; N 11.59. Calculated for $C_{13}H_{10}N_2O_3$: C 64.45; H 4.16; N 11.56.

T.L.C. eluant $CH_2Cl_2$:$CH_3OH$:$CH_3COOH$ (160:40:5).

Rf=0.4.

N.M.R. (DMSO-$d_6$) δp.p.m.: 5.32 (2H; s; —O—C$\underline{H}_2$), 6.90–8.10 (7H, m, aromatics+imidazole+

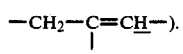

).

2-(3,4-dimethoxyphenyl)-3-(1-imidazolyl)-6-methoxy-2H-1-benzopyran

Analysis of the elements: Found C 69.00; H 5.49; N 7.61. Calculated for $C_{21}H_{20}N_2O_4$: C 69.22; H H 5.53; N 7.68.

T.L.C. eluant $CH_2Cl_2$:$CH_3OH$(180:20).

Rf=0.32.

ms: m/e: 364(M+, 100%); 349(M-15,20%); 296(M-68,17%); 281(296-15, 23%); 68 (92%).

3-(1-imidazolyl)-6-(2-carboxyisopropoxy)-2H-1-benzopyran;

3-(1-imidazolyl)-6-(2-carboxyvinyl)-2H-1-benzopyran;

2-methyl-3-(1-imidazolyl)-2H-1-benzopyran;

2-methyl-3-(1-imidazolyl)-6-hydroxy-2H-1-benzopyran;

2-methyl-3-(1-imidazolyl)-6-methoxy-2H-1-benzopyran;

2-methyl-3-(1-imidazolyl)-7-carboxy-2H-1-benzopyran;

2-methyl-3-(1-imidazolyl)-6-carbamoyl-2H-1-benzopyran;

2-methyl-3-(1-imidazolyl)-6-(2-carboxyvinyl)-2H-1-benzopyran;

2-methyl-3-(1-imidazolyl)-6-(2-carboxyisopropoxy)-2H-1-benzopyran;

2-methyl-3-(1-imidazolyl)-6-hydroxy-7-tert-butyl-2H-1-benzopyran;

2-iso-propyl-3-(1-imidazolyl)-6-carboxy-2H-1-benzopyran;

2-iso-propyl-3-(1-imidazolyl)-6-methoxy-2H-1-benzopyran;

2-cyclopropyl-3-(1-imidazolyl)-6-carboxy-2H-1-benzopyran;

2-(3,4-dihydroxyphenyl)-3-(1-imidazolyl)-6-hydroxy-2H-1-benzopyran;

2-(3-pyridyl)-3-(1-imidazolyl)-6-carboxy-2H-1-benzopyran;

3-(1-imidazolyl)-6-hydroxy-2H-1-benzopyran;

2-methyl-3-(1-imidazolyl)-6-ethoxycarbonyl-2H-1-benzopyran;

2-(4-hydroxyphenyl)-5,7-dihydroxy-2H-1-benzopyran; and 2-(3-pyridyl)-3-(1-imidazolyl)-6-methoxy-2H-1-benzopyran.

The 3-(1-imidazolyl)-2,3-dihydro-6-chloro-4H-1-benzopyran-4-ol used above was prepared as follows:

$NaBH_4$ (1 g) was added portionwise to a solution of 3-(1-imidazolyl)-2,3-dihydro-6-chloro-4H-1-benzopyran-4-one (2.7 g) in MeOH (70 ml) at 5°–10° C. The mixture, stirred at room temperature for 2 hours, added with water (300 ml), extracted with $CHCl_3$, dried and evaporated to dryness gave (2.7 g) 3-(1-imidazolyl)-2,3-dihydro-6-chloro-4H-1-benzopyran-4-ol.

Elemental analysis: Found: C 56.78; H 4.44; N 10.86; Cl 13.85. Calculated for $C_{12}H_{11}N_2O_2Cl$: C 57.48; H 4.42; N 11.17; Cl 14.14.

N.M.R. (pyridine-$d_5$) δp.p.m.: 4.26–5.00 (3H, m, —OC$\underline{H}_2$—CH—N>), 5.18 (1H, d, HO—C$\underline{H}$—), 6.96–8.12 (6H, m, aromatics+imidazole).

The 3-(1-imidazolyl)-2,3-dihydro-6-chloro-4H-1-benzopyran-4-one used above was prepared as follows:

a solution of 2-hydroxy-5-chloro-α-(1-imidazolyl)-acetophenone (2.4 g), paraformaldehyde (0.3 g) and acetic acid (45 ml) was refluxed for 30 minutes. The solvent was removed under reduced pressure, ethanol was added and the impurity traces were filtered off. The solvent was evaporated and the residue gave 2 g of 3-(1-imidazolyl)-2,3-dihydro-6-chloro-4H-1-benzopyran-4-one, m.p. 123°—125° C. (MeOH/$H_2O$).

N.M.R. (CDCl$_3$) δp.p.m.: 4.6–5.1 (2H, m, —O—C$\underline{H}_2$—CH>), 5.84 (1H, m, —O—CH$_2$—C$\underline{H}$), 6.92–7.84 (6H, m, aromatics+imidazole).

The 2-hydroxy-5-chloro-α-(1-imidazolyl)-acetophenone used above was prepared as follows:

a solution of 2-hydroxy-5-chloro-α-bromo-acetophenone (7 g), imidazole (6 g) and N,N-dimethylformamide (50 ml), was heated at 40° C. for 2 hours.

The solution was poured into ice-water and the solid, filtered off, gave 6 g of 2-hydroxy-5-chloro-α-(1-imidazolyl)-acetophenone, m.p. 201°–203° C. (ethanol).

EXAMPLE 2

7.8 g of 1,2,3,4-tetrahydro-2-(1-imidazolyl)-7-carboxy-1-naphthalenol were treated with glacial acetic acid (80 ml) and concentrated sulphuric acid (10 ml) and heated at 100° C. for 4 hours.

The reaction mixture was poured into 100 ml of ice-/water and the pH was adjusted to the neutrality by adding 35% NaOH. The precipitate was collected, filtered and washed with water, giving 6.7 g of 1,2-dihydro-3-(1-imidazolyl)-6-carboxy-naphthalene, m.p. 323°-6° C.

Elemental analysis: Found: C 69.32; H 4.96; N 11.51. Calculated for $C_{14}H_{12}N_2O_2$: C 69.98; H 5.03; N 11.65.

T.L.C.: eluant $CHCl_3$:$CH_3OH$:$CH_3COOH$ (45:5:2.5). Rf 0.45.

N.M.R. (CDCl$_3$, CF$_3$COOD) δp.p.m.: 2.8–3.4 (4H, m, —CH$_2$—CH$_2$—) 6.95 (1H, br s, —CH=C—), 7.38–8.89 (7H, m, COOH+aromatics+imidazole).

I.R. (KBr): νC=O 1685 cm$^{-1}$.

By proceeding analogously, the following compounds were prepared:

1,2-dihydro-3-(1-imidazolyl)-naphthalene

Elemental analysis: Found: C 78.3; H 6.22; N 13.95. Calculated for $C_{13}H_{12}N_2$: C 79.56; H 6.16; N 14.27.

T.L.C.: eluant $CH_2Cl_2$:$CH_3OH$ (170:30).

rf=0.71.

N.M.R. (CDCl$_3$) δp.p.m.: 2.6–3.1 (4H, m, —CH$_2$—CH$_2$—), 6.4 (1H, br s, —CH=C—), 7–7.8 (7H, m, aromatics+imidazole).

1,2-dihydro-3-(1-imidazolyl)-6-tert-butyl-7-hydroxy-naphthalene, m.p. 241°–243° C.

Elemental analysis: Found: C 75.43; H 7.39; N 9.95. Calculated for $C_{17}H_{20}N_2O$: C 76.08; H 7.51; N 10.43.

T.L.C.: eluant $CHCl_3$:$CH_3OH$ (180:20).

Rf=0.35.

N.M.R. (DMSO-$d_6$) δp.p.m.: 1.34 (9H, s, tert-butyl), 2.79 (4H, m, —CH$_2$—CH$_2$—), 6.70 (1H, s, —CH=C—), 6.61-8.06 (5H, m, aromatics+imidazole), 9.34 (1H, br s, —O$\underline{H}$).

1,2-dihydro-3-(1-imidazolyl)-7-carboxy-naphthalene collected as hydrochloride, m.p. 290°–295° C.

Elemental analysis: Found: C 60.50; H 4.80; N 10.05; Cl 12.65. Calculated for $C_{15}H_{13}ClN_2O_2$: C 60.87; H 4.71; N 10.10; Cl 12.70.

T.L.C.: eluant $CHCl_3:CH_3OH:CH_3COOH$ (80:20:5). Rf=0.6.

N.M.R. (DMSO) δp.p.m.: 3.04 (4H, m, $CH_2$—$CH_2$), 7.17 (1H, br s,

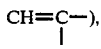

7.72–9.38 (6H, m, aromatics+imidazole).

1,2-dihydro-3-(1-imidazolyl)-6-(2-carboxyvinyl)-naphthalene

Elemental analysis: Found: C 72.71; H 5.26; N 10.65. Calculated for $C_{16}H_{14}N_2O_2$: C 72.18; H 5.26; N 10.56.

T.L.C.: eluant $CHCl_3:CH_3OH$ (90:10). Rf=0.30.

N.M.R. (DMSO-$d_6$) δp.p.m.: 2.8–3.2 (4H, m, $CH_2$—$CH_2$), 6.45 (1H, d,

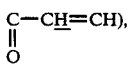

6.84 (1H, m s,

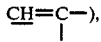

7.34 (1H, d,

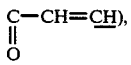

7.10–8.16 (6H, m, aromatics+imidazole).

1,2-dihydro-3-(1-imidazolyl)-6-hydroxy-7-acetyl-naphthalene, m.p. 135°–140° C.

Elemental analysis: Found: C 70.33; H 5.54; N 10.88. Calculated for $C_{15}H_{14}N_2O_2$: C 70.85; N 5.55; N 11.01.

T.L.C.: eluant $CHCl_3:CH_3OH$ (180:20). Rf=0.6.

N.M.R. (CDCl$_3$) δp.p.m.: 2.60 (3H, s, $CH_3$), 2.93 (4H m, $CH_2$—$CH_2$), 6.51 (1H, br s,

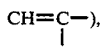

6.70–7.89 (5H, m, aromatics+imidazole), 12.33 (1H, br s, OH).

1,2-dihydro-3-(1-imidazolyl)-7-cyano-naphthalene

Elemental analysis: Found C 75.51; H 5.07; N 18.69. Calculated for $C_{14}H_{11}N_3$: C 76.01; H 4.98; N 19.00.

T.L.C.: eluant $CHCl_3:CH_3OH$ (90:10). Rf=0.45.

I.R. (KBr) ξC≡N 2220 cm$^{-1}$.

1,2-dihydro-3-(1-imidazolyl)-7-bromo-naphthalene

Elemental analysis: Found: C 56.55; H 3.95; N 10.16; Br 28.92. Calculated for $C_{13}H_{11}BrN_2$: C 56.73; H 4.00; N 10.18 Br 29.10.

T.L.C.: eluant $CHCl_3:CH_3OH$ (90:10). Rf=0.5.

N.M.R. (CDCl$_3$) δp.p.m.: 2.6–3.2 (4H, m, $CH_2$—$CH_2$), 6.45 (1H, br s,

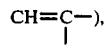

6.11–7.80 (7H, m, aromatics+imidazole).

1,2-dihydro-3-(1-imidazolyl)-6-methoxy-naphthalene, m.p. 63°–65° C.

Elemental analysis: Found: C 73.96; H 6.11; N 12.30. Calculated for $C_{14}H_{14}N_2O$: C 74.31; H 6.23; N 12.38.

T.L.C.: eluant $CHCl_3:CH_3OH$ (190:10). Rf=0.7.

N.M.R. (CDCl$_3$) δp.p.m.: 2.56–3.05 (4H, m, —$CH_2$—$CH_2$—), 3.72 (3H, s, —$OCH_3$), 6.41 (1H, dd, —CH=C—), 6.62–7.78 (6H, m, aromatics+imidazole).

1,2-dihydro-3-(1-imidazolyl)-5-bromo-6-methoxy-naphthalene, m.p. 140°–144° C.

Elemental analysis: Found: C 54.76; H 4.25; N 9.09; Br 26.02. Calculated for $C_{14}H_{13}BrN_2O$: C 55.1; H 4.29; N 9.18; Br 26.18.

T.L.C.: eluant $CHCl_3:CH_3OH$ (190:10). Rf=0.28.

N.M.R. (DMSO-$d_6$) δp.p.m.: 2.89 (4H, m, —$CH_2$—$CH_2$—), 3.82 (3H, s, —$OCH_3$), 6.96 (1H, br s,

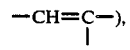

6.84–8.18 (5H, m, aromatics+imidazole).

1,2-dihydro-3-(1-imidazolyl)-7-methoxynaphthalene, m.p. 108°–110° C.

Elemental analysis: Found: C 73.79; H 6.09; N 12.19. Calculated for $C_{14}H_{14}N_2O$: C 74.31; H 6.23; N 12.38.

T.L.C.: eluant $CHCl_3:CH_3OH$ (195:5). Rf=0.3.

N.M.R. (CDCl$_3$) δp.p.m.: 2.5–3.2 (4H, m, $CH_2$—$CH_2$), 3.78 (3H, s, $OCH_3$), 6.47 (1H, s,

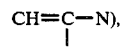

6.70–7.80 (6H, m, aromatics+imidazole).

1,2-dihydro-3-(1-imidazolyl)-8-methoxynaphthalene;
1,2-dihydro-3-(1-imidazolyl)-6-hydroxymethyl-naphthalene;
1,2-dihydro-3-(1-imidazolyl)-5-carboxy-naphthalene;
1,2-dihydro-3-(1-imidazolyl)-6-methoxy-7-bromo-naphthalene;
1,2-dihydro-3-(1-imidazolyl)-6-(2-ethoxycarbonylvinyl)-naphthalene;
1,2-dihydro-3-(1-imidazolyl)-65-carbamoyl-naphthalene;
1,2-dihydro-3-(1-imidazolyl)-6-hydroxy-7-carboxynaphthalene;
1,2-dihydro-3-(1-imidazolyl)-6-carboxymethylnaphthalene;
1,2-dihydro-3-(1-imidazolyl)-8-carboxy-naphthalene;
2-(1-imidazolyl)-5-carboxy-indene; and
2-(1-imidazolyl)-5-methoxy-indene.

The 1, 2, 3, 4-tetrahydro-2-(1-imidazolyl)-7-carboxy-1-naphthalenol used above was prepared by reducing 8 g of 2-(1-imidazolyl)-3,4-dihydro-7-carboxy-1-(2H)-naphthalenone with NaBH$_4$ (3.6 g) in methanol (200 ml). The reaction mixture was stirred at room temperature for 4 hours and then treated with 200 ml of water. The organic solvent was evaporated under vacuum and 8% HCl was added until pH 6. The precipitate was filtered and washed with ethyl acetate giving 7.8 g of product, m.p. 175° C.

Elemental analysis: Found: C 64.51; H 5.30; N 10.81. Calculated for $C_{14}H_{14}N_2O_3$: C 65.10; H 5.46; N 10.84.

N.M.R. (DMSO-$d_6$) δp.p.m.: 2.14 (2H, m, $CH_2$—$\underline{CH}_2$—CH—), 2.97 (2H, m, $\underline{CH_2}$—$CH_2$—CH—), 4.23 (1$\overline{H}$, dt, —CH—N—), 4.78 (1$\overline{H}$, d, —CH—OH), 6.10 (2H, br s, OH+COOH), 6.9-8.2 (6H, m, aromatics+imidazole).

The 2-(1-imidazolyl)-3,4-dihydro-7-carboxy-1-(2H)-naphthalenone used above was prepared as follows: 11.2 g of 2-bromo-3,4-dihydro-7-carboxy-1-(2H)-naphthalenone were dissolved in DMF (50 ml) and added dropwise at room temperature to a solution of imidazole (14 g) in DMF (70 ml).

After stirring at room temperature for 10 hours the organic solvent was evaporated under vacuum and the crude product was dissolved in ethanol (100 ml). By adding diethyl ether and filtering 8 g of 2-(1-imidazolyl)-3,4-dihydro-7-carboxy-1-(2H)-naphthalenone were obtained, m.p. >290° C.

I.R. (KBr) νC═O 1700 cm$^{-1}$.

N.M.R. (CF$_3$COOD) δp.p.m.: 2.92 (2H, m, $CH_2$—$\underline{CH_2}$—CH—), 3.52 (2H, m, $\underline{CH_2}$—$CH_2$—CH—), 5.67 (1$\overline{H}$, dd, —CH—), 7.57-8.83 (6H, m, aromatics+imidazole).

T.L.C.: eluant CH$_3$COCH$_3$/H$_2$O/CH$_3$COOH (90:10:5).

Rf=0.45.

The 2-bromo-3,4-dihydro-7-carboxy-1-(2H)-naphthalenone used above was prepared by reacting the known 3,4-dihydro-7-carboxy-1-(2H)-naphthalenone (8 g), with CuBr$_2$ (18.78 g) in ethyl acetate (400 ml).

The suspension was refluxed for 5 hours, then cooled and filtered. The solid was washed with ethyl acetate, the collected organic layers were washed with water, dried on anhydrous Na$_2$SO$_4$ and evaporated under vacuum, giving 8 g of product, m.p. 185° C.

Elemental analysis: Found: C 49.15; H 3.25; Br 29.51. Calculated for C$_{11}$H$_9$BrO$_3$: C 49.10; H 3.37; Br 29.69.

N.M.R. (CD$_3$COCD$_3$) δp.p.m.: 2.6 (2H, m, —CH$_2$—$\underline{CH_2}$—CH—), 3.2 (2H, m, —$\underline{CH_2}$—CH$_2$—CH—), 4.95 (1H, dd, —CH—), 7.53-8.63 (3H, m, aromatics).

EXAMPLE 3

A solution of 3,4-dihydro-2-(1-imidazolyl)-7-methoxy-1-naphthalenol (8 g) and conc. hydrobromic acid (140 ml) was heated at reflux for 8 hours.

The solution was poured in ice/water and the pH was made alkaline by Na$_2$CO$_3$. The solid precipitated was filtered, washed with water and dried.

The crude product was purified by elution on silica gel [solvent CHCl$_3$: CH$_3$OH (180:20)], obtaining 4.5 g of 1,2-dihydro-3-(1-imidazolyl)-6-hydroxy-naphthalene, m.p. 218°-220° C.

Elemental analysis:

Found: C 72.55; H 5.65; N 13.04. Calculated for C$_{13}$H$_{12}$N$_2$O: C 73.56; H 5.7; N 13.19.

T.L.C.: eluant CHCl$_3$: CH$_3$OH (180:20).

Rf=0.28.

N.M.R. (DMSO-$d_6$) δ p.p.m.: 2.82 (4.H, m, —$\underline{CH_2}$—CH$_2$—), 6.54-8.13 (6H, m, aromatics+imidazole), 6.61 (1H, br s,

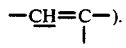

I.R. (KBr): ν max cm$^{-1}$, 3440 (OH phenolic), 2690 and 2610 (stretching NH+), 1645 (stretching C═C).

By proceeding analogously, the following compounds were prepared:

3-(1-imidazolyl)-2H-1-benzopyran, m.p. 50°-52° C.

Analysis of the elements: Found: C 71.98; H 5.03; N 14.01. Calculated for: C$_{12}$H$_{10}$N$_2$O: C 72.71; H 5.08; N 14.13.

T.L.C.: eluant CH$_2$Cl$_2$: CH$_3$OH (180:20).

Rf=0.5.

N.M.R. (CDCl$_3$) δ p.p.m.: 5.04 (2H, d, —O—CH$_2$), 6.50 (1H, br s,

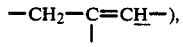

6.80-7.70 (7H, m, aromatics+imidazole).

1,2-dihydro-3-(1-imidazolyl)-6-carboxynaphthalene;
1,2-dihydro-3-(1-imidazolyl)-7-carboxynaphthalene;
1,2-dihydro-3-(1-imidazolyl)-5-carboxynaphthalene;
1,2-dihydro-3-(1-imidazolyl)-8-carboxynaphthalene; and
1,2-dihydro-3-(1-imidazolyl)-6-tert-butyl-7-hydroxy-naphthalene.

The 3,4-dihydro-2-(1-imidazolyl)-7-methoxy-1-naphthalenol used above was prepared by reduction of the 3,4-dihydro-2-(1-imidazolyl)-7-methoxy-1-(2H)-naphthalenone with NaBH$_4$ following the same method described in the Example 2 for the 7-carboxy derivative; m.p. 159°-162° C.

Elemental analysis: Found: C 68.55; H 6.84; N 11.40. Calculated for C$_{14}$H$_{16}$N$_2$O$_2$: C 68.83; H 6.6; N 11.46.

T.L.C. eluant CHCl$_3$: CH$_3$OH (180:20).

Rf=0.3.

N.M.R. (CDCl$_3$) δ p.p.m.: 1.95-2.70 (2H, m, —CH$_2$—$\underline{CH_2}$—CH—, ) 2.91 (2H, m, $\underline{CH_2}$—CH$_2$—CH—), 3.79 (3H, s, $\underline{OCH_3}$), 3.88-4.40 (1$\overline{H}$, m, —CH—N—), 4.72-6.20 (1$\overline{H}$, m, —CH—OH), 6.20 (1H, br s, OH), 6.64-7.50 (6H, m, aromatics+imidazole).

The 3,4-dihydro-2-(1-imidazolyl)-7-methoxy-1-(2H)-naphthalenone used above was prepared from the 3,4-dihydro-2-bromo-7-methoxy-1-(2H)-naphthalenone and imidazole following the same method described in the Example 2; m.p. 115°-116° C.

Elemental analysis: Found: C 69.44; H 5.82; N 11.59. Calculated for C$_{14}$H$_{14}$N$_2$O$_2$: C 69.40; H 5.82; N 11.56.

T.L.C.: eluant CHCl$_3$: CH$_3$OH (180:20).

Rf=0.55.

N.M.R. (CDCl$_3$) δ p.p.m.: 2.42-2.72 (2H, m, CH$_2$—$\underline{CH_2}$—CH—), 3.02-3.35 (2H, m, $\underline{CH_2}$—CH$_2$—CH—), 3.84 (3H, s, $\underline{OCH_3}$), 4.96 (1H, $\overline{dd}$, —CH—), 6.96-7.58 (6H, aromatics+imidazole).

I.R. (KBr) ν C═O 1700 cm$^{-1}$.

The 3,4-dihydro-2-bromo-7-methoxy-1-(2H)-naphthalenone used above was obtained by bromination with CuBr$_2$ of the known 3,4-dihydro-7-methoxy-1-(2H)-naphthalenone, following the same procedure described in the Example 2; m.p. 78°-80° C.

T.L.C.: eluant CHCl$_3$: CH$_3$OH (170:30).

Rf=0.55.

N.M.R. (CDCl$_3$) δ p.p.m.: 2.45 (2H, m, —CH$_2$—$\underline{CH_2}$— —CH—), 2.95 (2H, m, —$\underline{CH_2}$—CH$_2$—

—CH—), 3.78 (3H, s, —OCH₃), 4.66 (1H, dd, —CH—), 6.91–7.49 (3H, m, aromatics).

EXAMPLE 4

A solution of 3-(1-imidazolyl)-2,3-dihydro-6-methoxy-4H-1-benzopyran-4-one (0.5 g) in ethanol (50 ml), glacial acetic acid (20 ml) and concentrated sulphuric acid (5 ml) was hydrogenated in the presence of 100 mg of Pd 10% on activated carbon at 3.42 atm, at 80° C. for 8 hours.

The catalyst was filtered off, the acid solution, neutralized with NH₄OH, extracted with CH₂Cl₂, dried and evaporated, gave 0.3 g of 3,4-dihydro-3-(1-imidazolyl)-6-methoxy-1-benzopyran.

Elemental analysis:
Found: C 67.1; H 6.08; N 12.08 Calculated for C₁₃H₁₄N₂O₂: C 67.8; H 6.13; N 12.16

N.M.R. (CDCl₃) δ p.p.m.: 3.10 (1H, dd,

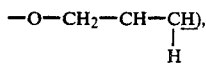

3.42 (1H, dd,

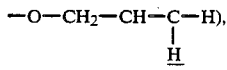

3.80 (3H, s, —O—CH₃), 4.10–4.25 (2H, m, —O—CH₂—CH—), 4.67 (1H, m, —O—CH₂—CH—), 6.60–7.64 (6H, m, aromatics+imidazole).

Analogously, the following compounds were prepared:
3,4-dihydro-3-(1-imidazolyl)-6-carboxy-1-benzopyran;
1,2,3,4-tetrahydro-2-(1-imidazolyl)-7-carboxy-naphthalene;
1,2,3,4-tetrahydro-2-(1-imidazolyl)-6-carboxy-naphthalene; and
1,2,3,4-tetrahydro-2-(1-imidazolyl)-7-methoxy-naphthalene.

The 3-(1-imidazolyl)-2,3-dihydro-6-methoxy-4H-1-benzopyran-4-one used above was prepared as follows: a solution of 3-bromo-6-methoxy-2,3-dihydro-4H-1-benzopyran-4-one (7 g), imidazole (8 g), and N,N-dimethylformamide (200 ml), was kept at 60° C. for 5 hours. The solvent was evaporated under reduced pressure and the residue, taken up with CH₂Cl₂ (100 ml), washed with H₂O, was extracted with a solution of 8% HCl. The acidic solution, neutralized with NaHCO₃, extracted with CH₂Cl₂, dried and evaporated, gave 2 g of 3-(1-imidazolyl)-2,3-dihydro-6-methoxy-4H-1-benzopyran-4-one, m.p. 150°–152° C. (EtOH 70%).

N.M.R. (CDCl₃) δ p.p.m.: 3.85 (3H, s, —O—CH₃), 4.7 (2H, m, —O—CH₂—CH>), 5.04 (1H, m, —O—CH₂—CH>), 6.9–7.6 (6H, m, aromatics+imidazole).

EXAMPLE 5

A mixture of 1,2-dihydro-3-(1-imidazolyl)-6-carboxy-naphthalene (1.6 g), palladium 10% on activated carbon (0.3 g), ethanol 99% (70 ml), glacial acetic acid (30 ml) and concentrated hydrochloric acid (5 ml) was hydrogenated for 12 hours at room temperature in a Parr-Burgess low pressure hydrogenator at an initial pressure of 3.42 atm.

At the end of this time 96% of the theoretical amount of hydrogen had been absorbed.

Filtering the catalyst, evaporating the solvent and treating with water (50 ml) gave 1.3 g of 1,2,3,4-tetrahydro-2-(1-imidazolyl)-7-carboxy-naphthalene hydrochloride, m.p. 280° C.

Elemental analysis: Found: C 60.08; H 5.37; N 9.85; Cl 12.54. Calculated for C₁₄H₁₅ClN₂O₂: C 60.32; H 5.42; N 10.05; Cl 12.72.

T.L.C.: eluant CHCl₃: CH₃OH: CH₃COOH (170:30:1.5).
Rf=0.26.

N.M.R. (DMSO-d₆) δ p.p.m.: 2.34 (2H, m, CH₂—CH₂—CH—), 3.03 (2H, m, CH₂—CH₂—CH—), 3.38 (2H, m,

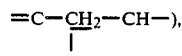

4.88 (1H, m, CH₂CH—CH₂—), 7.30–9.30 (7H, m, COOH+aromatics+imidazole).

I.R. (KBr) ν C=O 1690 cm⁻¹.

By proceeding analogously, the following compounds were prepared:
cis-3,4-dihydro-2-methyl-3-(1-imidazolyl)-6-carboxy-1-benzopyran-hydrochloride, m.p. 228°–235° C.

Elemental analysis: Found: C 56.2; H 5.23; N 9.10; Cl⁻11.89. Calculated for C₁₄H₁₄N₂O₃·HCl: C 57.05; H 5.13; N 9.50; Cl⁻ 12.02.

N.M.R. (CDCl₃) δ p.p.m. 1.17 (3H, d, —CH₃), 3.25–3.67 (2H, m, —O—CH—CH—CH₂), 4.70 (1H, m, —O—CH—CH—), 5.23 (1H, m, —O—CH—CH—), 6.98–9.10 (6H, m, aromatics+imidazole).

I.R. (KBr) ν (NH⁺) 2800–2300 cm⁻¹, (OH) carboxylic acid 3000–2300 cm⁻¹, (C=O) carboxylic acid 1700 cm⁻¹, (C—O—C) 1250 cm⁻¹.

1,2,3,4-tetrahydro-2-(1-imidazolyl)-naphthalene hydrochloride, which treated with the stoichiometric amount of NaHCO₃, gave 1,2,3,4-tetrahydro-2-(1-imidazolyl)naphthalene, m.p. 95°–98° C.

Elemental analysis: Found: C 78.26; H 7.16; N 13.81. Calculated for C₁₃H₁₄N₂: C 78.75; H 7.11; N 14.12.

T.L.C.: eluant CH₂Cl₂: CH₃OH (170:30).
Rf=0.57.

N.M.R. (CDCl₃) δ p.p.m.: 1.97–2.5 (2H, m, =C—CH₂—CH—CH₂— —CH₂—), 2.96 (2H, m, =C—CH₂—CH—CH₂—CH₂—), 3.26 (2H, m, =C—CH₂—CH—CH₂—CH₂—), 4.46 (1H, m, =C—CH₂—CH—CH₂—CH₂—), 7.03–7.62 (7H, m, aromatics+imidazole).

1,2,3,4-tetrahydro-2-(1-imidazolyl)-7-methoxy-naphthalene hydrochloride which treated with the stoichiometric amount of NaHCO₃ gave 1,2,3,4-tetrahydro-2-(1-imidazolyl)-7-methoxy-naphthalene.

Elemental analysis: Found: C 73.14; H 6.95; H 12.21. Calculated for C₁₄H₁₆N₂O: C 73.65; H 7.06; N 12.27.

T.L.C.: eluant CHCl₃: CH₃OH (190:10).
Rf=0.31.

N.M.R. (CDCl₃) δ p.p.m.: 2.22 (2H, m, CH₂—CH₂—CH—), 2.88 (2H, m, CH₂—CH₂—CH—), 3.20 (2H, m, —CH₂—CH—), 3.76 (3H, s, CH₃O—), 4.40 (1H, m, —CH—), 6.61–7.78 (6H, m, aromatics+imidazole) and analogously after treatment with the stoichiometric amount of NaHCO₃ the following compounds were obtained:
3,4-dihydro-3-(1-imidazolyl)-6-methoxy-1-benzopyran;
3,4-dihydro-3-(1-imidazolyl)-6-carboxy-1-benzopyran;

3,4-dihydro-2-(3-pyridyl)-3-(1-imidazolyl)-6-carboxy-1-benzopyran;
1,2,3,4-tetrahydro-2-(1-imidazolyl)-6-carboxy-naphthalene;
1,2,3,4-tetrahydro-2-(1-imidazolyl)-7-(2-carboxyisopropoxy)-naphthalene;
2-(1-imidazolyl)-5-carboxy-indan;
2-(1-imidazolyl)-5-carboxymethyloxy-indan; and
1,2,3,4-tetrahydro-2-(1-imidazolyl)-7-carboxymethyl-naphthalene.

EXAMPLE 6

A mixture of 1,2-dihydro-3-(1-imidazolyl)-6-hydroxynaphthalene (1.85 g), potassium tert-butoxide (1.17 g), ethylbromoacetate (1.12 ml) and tert-butanol (50 ml) was refluxed for 4 hours.

The organic solvent was evaporated under vacuum and the residue treated with water (100 ml) and $CH_2Cl_2$ (100 ml). The organic layer was separated and washed with brine, dried on anhydrous $Na_2SO_4$ and evaporated under reduced pressure. The crude product was purified by elution on silica gel (solvent; $CHCl_3$: $CH_3OH$—180:20) giving 2.6 g of 1.2-dihydro-3-(1-imidazolyl)-6-ethoxycarbonylmethyloxynaphthalene, oil.

Elemental analysis: Found: C 68.35; H 6.81; N 9.35. Calculated for $C_{17}H_{18}N_2O_3$: C 68.44; H 6.88; N 9.39.

N.M.R. ($CDCl_3$) δ p.p.m.: 1.29 (3H, t, $\underline{CH_3}$—$CH_2$—), 2.6-3.1 (4H, m, $\underline{CH_2}$—$\underline{CH_2}$—CH—), 4.24 (2H, q, $\underline{CH_2}$—$CH_3$), 4.58 ($\overline{2H}$, s, O—$CH_2$—COO), 6.44 (1H, br s, —$\underline{CH}$=C—), 6.67-7.80 (6H, m, aromatics+imidazole).

Analogously, the following compounds were prepared:
1,2-dihydro-3-(1-imidazolyl)-6-(2-ethoxycarbonylisopropoxy)-naphthalene
T.L.C.: eluant $CHCl_3$: $CH_3OH$(180:20).
Rf=0.75.
N.M.R. ($CDCl_3$) δ p.p.m.: 1.25 (3H, t, $\underline{CH_3}$—$CH_2$), 1.57 (6H, s, $(\underline{CH_3})_2C>$), 2.63-3.1—(4H, m, —$CH_2$—$CH_2$), 4.23 ($\overline{2H}$, q, —$CH_2$—$CH_3$), 6.41 (1H, br s, —$\underline{CH}$=C—), 6.63-7.80 (6H, m, aromatics+imidazole).

Analogously, by reaction with α-bromoisobutyric acid, the following compound was prepared:
1,2-dihydro-3-(1-imidazolyl)-6-(2-carboxyisopropoxy)-naphthalene.

EXAMPLE 7

A solution of 1,2-dihydro-3-(1-imidazolyl)-6-ethoxycarbonylmethyloxy-naphthalene (1 g) and methanolic potassium hydroxide N/2 (25 ml) was refluxed for 4 hours. The organic solvent was evaporated under vacuum and the residue dissolved in water (100 ml).

Acidification with acetic acid, filtration of the solid precipitated and washing with water gave 800 mg of 1,2-dihydro-3-(1-imidazolyl)-6-carboxymethyloxynaphthalene m.p. 106°-108° C. (dec.).

Elemental analysis: Found: C 66.53; H 5.21; N 10.25. Calculated for $C_{15}H_{14}N_2O_3$: C 66.65; H 5.22; N 10.36.
T.L.C.: eluant $CHCl_3$: $CH_3OH$: $CH_3COOH$ (40:10:2.5).
RF=0.36.
N.M.R. (DMSO-$d_6$) δ p.p.m.: 2.85 (5H, br s, —$CH_2$—$CH_2$), 4.65 (2H, s, O—$\underline{CH_2}$—COOH—), 6.80 (1H, br s, —$\underline{CH}$=C—), 6.68-8.15 (6H, m, aromatics+imidazole).
I.R. (KBr) ν C=O 1735 $cm^{-1}$.
By proceeding analogously the following compounds were obtained:

1,2-dihydro-3-(1-imidazolyl)-6-(2-carboxyisopropoxy)-naphthalene, m.p. 206°-209° C.
Elemental analysis: Found: C 68.05; H 6.11; N 8.97. Calculated for $C_{17}H_{18}N_2O_3$: C 68.46; H 6.08; N 9.39.
T.L.C.: eluant $CHCl_3$: $CH_3OH$:$CH_3COOH$ (40:10:2.5).
Rf=0.69.
N.M.R. (DMSO-$d_6$) δ p.p.m.: 1.50 (6H, s, $(CH_3)_2$—C—), 2.85 (4H, br s, —$CH_2$—$CH_2$—), 6.65 (1H, br s, —$\underline{CH}$=C—), 6.60-8.11 (6H, m, aromatics+imidazole).

3-(1-imidazolyl)-6-carboxy-2H-1-benzopyran;
3-(1-imidazolyl)-6-(2-carboxyisopropoxy)-2H-1-benzopyran;
3-(1-imidazolyl)-6-(2-carboxyvinyl)-2H-1-benzopyran;
2-methyl-3-(1-imidazolyl)-6-carboxy-2H-1-benzopyran;
2-methyl-3-(1-imidazolyl)-7-carboxy-2H-1-benzopyran;
2-methyl-3-(1-imidazolyl)-6-(2-carboxyvinyl)-2H-1-benzopyran;
2-methyl-3-(1-imidazolyl)-6-(2-carboxyisopropoxy)-2H-1-benzopyran;
2-iso-propyl-3-(1-imidazolyl)-6-carboxy-2H-1-benzopyran;
2-cyclopropyl-3-(1-imidazolyl)-6-carboxy-2H-1-benzopyran;
2-(3-pyridyl)-3-(1-imidazolyl)-6-carboxy-2H-1-benzopyran;
3,4-dihydro-3-(1-imidazolyl)-6-carboxy-1-benzopyran;
3,4-dihydro-2-methyl-3-(1-imidazolyl)-6-carboxy-1-benzopyran;
3,4-dihydro-2-methyl-3-(1-imidazolyl)-6-(2-carboxyvinyl)-1-benzopyran;
3,4-dihydro-2-(3-pyridyl)-3-(1-imidazolyl)-6-carboxy-1-benzopyran;
1,2-dihydro-3-(1-imidazolyl)-7-carboxy-naphthalene;
1,2-dihydro-3-(1-imidazolyl)-5-carboxy-naphthalene;
1,2-dihydro-3-(1-imidazolyl)-6-carboxynaphthalene;
1,2-dihydro-3-(1-imidazolyl)-8-carboxynaphthalene;
1,2-dihydro-3-(1-imidazolyl)-6-(2-carboxyvinyl)-naphthalene;
1,2,3,4-tetrahydro-2-(1-imidazolyl)-7-carboxy-napthalene;
1,2,3,4-tetrahydro-2-(1-imidazolyl)-6-carboxy-naphthalene;
1,2,3,4-tetrahydro-2-(1-imidazolyl)-7-(2-carboxyisopropoxy)-naphthalene;
1,2,3,4-tetrahydro-2-(1-imidazolyl)-7-(2-carboxyvinyl)-naphthalene;
1,2,3,4-tetrahydro-2-(1-imidazolyl)-7-carboxymethyl-naphthalene;
2-(1-imidazolyl)-5-carboxy-indene;
2-(1-imidazolyl)-5-(2-carboxyvinyl)-indene; and
2-(1-imidazolyl)-5-carboxy-indan.

EXAMPLE 8

EtOH absolute (14.4 ml) was added slowly to $SOCl_2$(2.2 ml) at 0° C. and the mixture was heated at room temperature and 1,2-dihydro-3-(1-imidazolyl)-6-carboxy-naphthalene (7 g) was added. The reaction mixture was refluxed for one day, then was stirred overnight at room temperature. The solvent and the excess of $SOCl_2$ were evaporated under reduced pressure and the residue was chromatographed on silica gel using $CHCl_3$:$CH_3OH$ (50:5) as eluant to give 1,2-dihydro-3-(1-imidazolyl)-6-ethoxycarbonyl-naphthalene(6.8 g), m.p. 113°-116° C.

Elemental analysis: Found: C 71.50; H 5.82; N 10.50. Calculated for $C_{16}H_{16}N_2O_3$: C 71.64; H 5.97; N 10.45.

T.L.C.: eluant CHCl₃: CH₃OH (50:5).
N.M.R. (CDCl₃)δp.p.m.: 1.62 (3H, t, CH₃—CH₂—), 2.80-3.40 (4H, m,

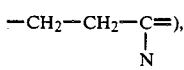

4.39 (2H, q,

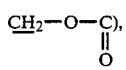

6.92 (1H, s, —CH═), 7.28-8 (6H, m, aromatics+imidazole).

Analogously, the following compound was prepared:
1,2-dihydro-3-(1-imidazolyl)-6-(2-ethoxycarbonyl-vinyl)naphthalene Elemental analysis: Found: C 72.81; H 6.07; N 9.45. Calculated for C₁₈H₁₈N₂O₂: C 73.47; H 6.12; N 9.52.

T.L.C.: eluant CHCl₃: CH₃OH (90:10).
Rf=0.48.

N.M.R. (CDCl₃)δp.p.m.: 1.33 (3H, t, CH₃), 2.65-3.20 (4H, m, CH₂—CH₂), 4.26 (2H, q, CH₂—CH₃), 6.40 (1H, d, CH═CH—COO), 6.55 (1H, br s,

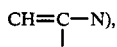

7.1-7.9 (6H, m, aromatics+imidazole), 7.62 (1H, d, CH═CH—COO).

EXAMPLE 9

To a suspension of 1,2-dihydro-3-(1-imidazolyl)-6-carboxy-naphthalene (500 mg) in DMF (10 ml) SOCl₂ (2 ml) was added. Cooling in an ice bath, NH₃ was passed through the reaction mixture, with stirring, for 4 hours. The reaction mixture was allowed to stand for 12 hours. The ammonium salt was filtered off and Et₂O was added giving a precipitate which was chromatographed on silica gel with CHCl₃:CH₃OH-CH₃COOH (45:5:2.5) as eluant; 350 mg of 1,2-dihydro-3-(1-imidazolyl)-6-carbamoyl-naphthalene were obtained.

T.L.C.: eluant CHCl₃:CH₃OH (50:5).
N.M.R. (CD₃OH)δp.p.m. 2.88 (2H, t, CH₂—CH₂—C═) 3.11 (2H, t, CH₂—CH₂—C═), 6.78 (1H, s, —CH═), 7.06-8.06 (6H, m, aromatics+imidazole).
I.R. (KBr)ν max cm⁻¹ 1670 (C═O) 3520-3410 (N—H).
M.S. m/e 239 (M+).

By proceeding analogously the following compounds was prepared:
2-methyl-3-(1-imidazolyl)-6-carbamoyl-2H-1-benzopyran.

EXAMPLE 10

To a suspension of LiAlH₄ (202 mg) in dry THF (2.4 ml) a solution of 1,2-dihydro-3-(1-imidazolyl)-6-ethoxycarbonyl-naphthalene (2.8 g) in dry THF (22 ml) was added dropwise at 0° C. under nitrogen atmosphere. The reaction mixture was refluxed for 1 day and then stirred overnight at room temperature. H₂O (40 ml) was added and the precipitate formed filtered off. The filtrate was concentrated, extracted with CHCl₃, dried (Na₂SO₄) and evaporated under vacuum to give 1,2-dihydro-3-(1-imidazolyl)-6-hydroxymethyl-naphthalene (2 g), m.p. 88°-91° C.

Elemental analysis: Found: C 74.00; H 6.13; N 12.03. Calculated for C₁₄H₁₄N₂O: C 74.33; H 6.19; N 12.39.

T.L.C.: eluant CHCl₃: CH₃OH (50:5).
N.M.R. (CDCl₃) p.p.m.: 2.80 (4H, m, CH₂—CH₂), 4.60 (2H, s, CH₂—OH), 5.26 (1H, s, —OH), 6.40 (1H, s, —CH═), 7.08-7.63 (6H, m, aromatics+imidazole).

EXAMPLE 11

1,2-dihydro-3-(1-imidazolyl)-6-methoxy-naphthalene was treated with a stoichiometric amount of hydrogen chloride, to give 1,2-dihydro-3-(1-imidazolyl)-6-methoxy-naphthalene hydrochloride, m.p. 70°-72° C.

T.L.C.: eluant CHCl₃:CH₃OH (180:20).
Rf=0.61.
N.M.R. (DMSO-d₆)δp.p.m.: 2.92 (4H, m, CH₂—CH₂), 7.10 (1H, br s, —CH═C—), 6.77-8.27 (6H, m, aromatics+imidazole), 9.65 (1H, br s, H+).

EXAMPLE 12

Tablets, each weighing 150 mg and containing 50 mg of the active substance were manufactured as follows:

| Compositions (for 10,000 tablets.) | |
| --- | --- |
| 1,2-dihydro-3-(1-imidazolyl)-6-carboxy-naphthalene | 500 g |
| Lactose | 710 g |
| Corn starch | 237.5 g |
| Talc powder | 37.5 g |
| Magnesium stearate | 15 g |

1,2-dihydro-3-(1-imidazolyl)-6-carboxy-naphthalene; lactose and a half of the corn starch were mixed; the mixture was then forced through a sieve of 0.5 mm openings. Corn starch (18 g) was suspended in warm water (180 ml). The resulting paste was used to granulate the powder. The granules were dried, comminuted on a sieve of sieve size 1.4 mm, then the remaining quantity of starch, talc and magnesium was added, carefully mixed, and processed into tablets using punches of 8 mm diameter.

We claim:

1. A compound of general formula (I)

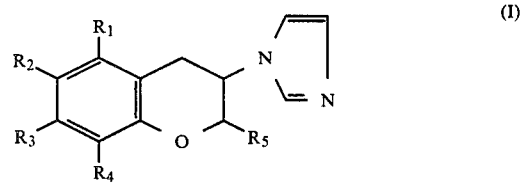

wherein
the symbol represents a single or a double bond;
each of R₁, R₂, R₃ and R₄, which may be the same or different, is
(a) hydrogen; hydroxy; halogen; cyano; C₁-C₆ alkyl; C₁-C₆ alkoxy; a C₂-C₄ acyl or C₂-C₄ acylamino group; —SR',

—CH$_2$OR', —COR or —CH$_2$COR, wherein R is —OR' or

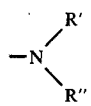

and each of R' and R", being the same or different, is hydrogen or C$_1$–C$_6$ alkyl; or
(b) one of R$_1$, R$_2$, R$_3$ and R$_4$ is 5-tetrazolyl or a group selected from —COCH$_2$OR',

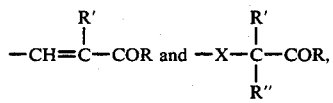

wherein R, R' and R" are as defined above, and X is —O—, —S— or —NH—, and the others are as defined above under (a);
R$_5$ is hydrogen, C$_1$–C$_6$ alkyl, C$_3$–C$_6$ cycloalkyl, or a phenyl or 3-pyridyl ring, wherein the phenyl or pyridyl ring is unsubstituted or substituted by one to three substituents chosen from hydroxy and C$_1$–C$_4$ alkoxy; or a pharmaceutically acceptable salt thereof.

2. A compound of claim 1, wherein
the symbol       represents a double bond;
each of R$_1$, R$_2$, R$_3$ and R$_4$, which may be the same or different, is
(a') hydrogen, hydroxy, halogen, C$_1$–C$_4$ alkyl, C$_1$–C$_4$ alkoxy, —CH$_2$OH, —COOR$_a$ or

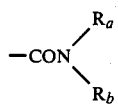

wherein each of R$_a$ and R$_b$ is independently hydrogen, or C$_1$–C$_4$ alkyl; or
(b') one of R$_1$, R$_2$, R$_3$ and R$_4$ is C$_2$–C$_4$ acyl, —CH$_2$COOR$_a$,

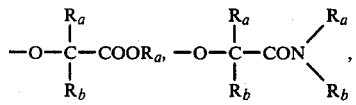

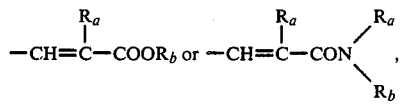

wherein R$_a$ and R$_b$ are as defined above, and the others are as defined above under (a'):
R$_5$ is hydrogen, and the other is hydrogen, C$_1$–C$_3$ alkyl, cyclopropyl, or a phenyl or 3-pyridyl ring unsubstituted or substituted by one to three substituents chosen from hydroxy and C$_1$–C$_2$ alkoxy; or a pharmaceutically acceptable salt thereof.

3. A compound of claim 1 wherein
the symbol       represents a double bond;
one of R$_1$, R$_2$, R$_3$ and R$_4$ is —COOR$_a$, wherein R$_a$ is as defined in claim 2, and the others are independently chosen from hydrogen and hydroxy;
or one of R$_1$, R$_2$, R$_3$ and R$_4$ is —CONH$_2$, —CH$_2$OH, —COCH$_3$, —CH$_2$COOR$_a$,

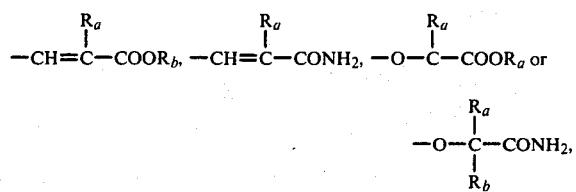

wherein R$_a$ and R$_b$ are as defined in claim 2, and the others are hydrogen;
R$_5$ is hydrogen; or a pharmaceutically acceptable salt thereof.

4. A compound of claim 1, wherein
the symbol       represents a double bond;
one of R$_1$, R$_2$, R$_3$ and R$_4$ is

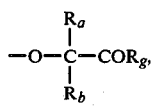

wherein R$_g$ is is —NH$_2$ or —OR$_a$ and R$_a$ and R$_b$ are independently hydrogen or C$_1$–C$_4$ alkyl, and the others are hydrogen;
R$_5$ is hydrogen; or a pharmaceutically acceptable salt thereof.

5. A compound selected from the group consisting of:
3-(1-imidazolyl)-2H-1-benzopyran;
3-(1-imidazolyl)-6-chloro-2H-1-benzopyran;
3-(1-imidazolyl)-6-methoxy-2H-1-benzopyran;
3-(1-imidazolyl)-6-carboxy-2H-1-benzopyran;
3-(1-imidazolyl)-6-(2-carboxyisopropoxy)-2H-1-benzopyran;
3-(1-imidazolyl)-6-(2-carboxyvinyl)-2H-1-benzopyran;
2-methyl-3-(1-imidazolyl)-6-methoxy-2H-1-benzopyran;
2-methyl-3-(1-imidazolyl)-6-carboxy-2H-1-benzopyran;
2-methyl-3-(1-imidazolyl)-7-carboxy-2H-1-benzopyran;
2-methyl-3-(1-imidazolyl)-6-carbamoyl-2H-1-benzopyran;
2-methyl-3-(1-imidazolyl)-6-(2-carboxyvinyl)-2H-1-benzopyran;
2-methyl-3-(1-imidazolyl)-6-(2-carboxyisopropoxy)-2H-1-benzopyran;
2-isopropyl-3-(1-imidazolyl)-6-carboxy-2H-1-benzopyran;
2-methyl-3-(1-imidazolyl)-6-ethoxycarbonyl-2H-1-benzopyran;
2-cyclopropyl-3-(1-imidazolyl)-6-carboxyl-2H-1-benzopyran;
2-(3,4-dimethoxyphenyl)-3-(1-imidazolyl)-6-methoxy-2H-1-benzopyran;
2-(3,4-dihydroxyphenyl)-3-(1-imidazolyl)-6-hydroxy-2H-1-benzopyran;
2-(3-pyridyl)-3-(1-imidazolyl)-6-carboxy-2H-1-benzopyran;
2-(4-hydroxyphenyl)-3-(1-imidazolyl)-5,7-dihydroxy-2H-1-benzopyran;
3,4-dihydro-3-(1-imidazolyl)-6-carboxy-1-benzopyran;
3,4-dihydro-2-methyl-3-(1-imidazolyl)-6-carboxy-1-benzopyran;
3,4-dihydro-2-methyl-3-(1-imidazolyl)-6-(2-carboxyvinyl)-1-benzopyran; or
a pharmaceutically acceptable salt thereof, or, when appropriate, a C$_1$–C$_4$ alkyl ester thereof.

6. A pharmaceutical composition for inducing vasodilation comprising a suitable carrier or diluent and a vasodilatory effective amount of the compound as claimed in claim 1.

7. A pharmaceutical composition for inhibiting blood platelete aggregation comprising a suitable carrier or diluent and a blood platelet antiaggregatory effective amount of the compound as claimed in claim 1.

8. A pharmaceutical composition for the treatment of migraine comprising a suitable carrier or diluent and a therapeutically effective amount of the compound as claimed in claim 1.

9. A pharmaceutical composition for the treatment of diabetic microangiopathy comprising a suitable carrier or diluent and a therapeutically effective amount of the compound as claimed in claim 1.

10. A pharmaceutical composition for the treatment of rheumatoid arthritis comprising a suitable carrier or diluent and a therapeutically effective amount of the compound as claimed in claim 1.

11. A pharmaceutical composition for the treatment of hypertension comprising a suitable carrier or diluent and a therapeutically effective amount of the compound as claimed in claim 1.

12. A pharmaceutical composition for the treatment of peptic ulcers comprising a suitable carrier or diluent and a therapeutically effective amount of the compound as claimed in claim 1.

13. A pharmaceutical composition for the treatment of osteoporosis comprising a suitable carrier or diluent and a therapeutically effective amount of the compound as claimed in claim 1.

14. A pharmaceutical composition for the treatment of angina pectoris comprising a suitable carrier or diluent and a therapeutically effective amount of the compound as claimed in claim 1.

15. A pharmaceutical composition for the treatment of atherosclerosis comprising a suitable carrier or diluent and a therapeutically effective amount of the compound as claimed in claim 1.

16. A pharmaceutical composition for the treatment of dislipidaemies comprising a suitable carrier or diluent and a therapeutically effective amount of the compound as claimed in claim 1.

17. A method of treating atherosclerosis in a patient comprising administering to the patient a therapeutically effective amount of the compound as claimed in claim 1.

18. A method of treating dislipidaemics in a patient comprising administering to the patient a therapeutically effective amount of the compound as claimed in claim 1.

* * * * *

UNITED STATES PATENT AND TRADEMARK OFFICE
CERTIFICATE OF CORRECTION

PATENT NO. : 4,602,022

DATED : July 22, 1986

INVENTOR(S) : Paolo Cozzi et al.

Page 1 of 3

It is certified that error appears in the above-identified patent and that said Letters Patent is hereby corrected as shown below:

In the Abstract, second line after the structural formula, delete "--------" and insert therefor -- ---- --.

Column 1, line 60, delete "--------" and insert therefor -- ---- --.

Column 4, line 62, delete "------" and insert therefor -- ---- --.

Column 5, line 31, after "symbol", insert -- ---- --.

Column 5, line 54, delete "--------" and insert therefor -- ---- --.

Column 6, line 1, after "symbol" insert -- ---- -- .

Column 6, line 18, after "symbol", insert -- ---- --.

UNITED STATES PATENT AND TRADEMARK OFFICE
CERTIFICATE OF CORRECTION

PATENT NO. : 4,602,022  
DATED : July 22, 1986  
INVENTOR(S) : Paolo Cozzi, et al.

Page 2 of 3

It is certified that error appears in the above-identified patent and that said Letters Patent is hereby corrected as shown below:

Column 9, lines 61 and 66, each occurrence, delete "--------" and insert -- ____ --.

Column 10, lines 38 and 53, each occurrence, delete "--------" and insert -- ____ --.

Column 16, line 48, before "represents", insert -- ____ --.

Claim 1, column 36, lines 47-53, delete the structural formula in its entirety and insert therefor

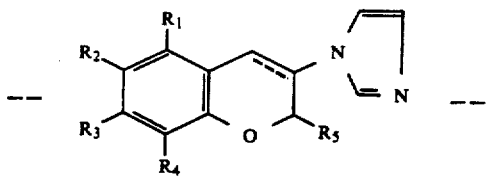

Claim 1, column 36, line 56, after "symbol", insert -- ____ --.

Claim 2, column 37, line 29, after "symbol", insert -- ____ --.

UNITED STATES PATENT AND TRADEMARK OFFICE
CERTIFICATE OF CORRECTION

PATENT NO. : 4,602,022

DATED : July 22, 1986

INVENTOR(S) : Paolo Cozzi, et al.

It is certified that error appears in the above-identified patent and that said Letters Patent is hereby corrected as shown below:

Claim 3, column 37, line 63, after "symbol", insert -- ---- --.

Claim 4, column 38, line 16, after "symbol", insert -- ---- --.

Signed and Sealed this

Third Day of March, 1987

*Attest:*

DONALD J. QUIGG

*Attesting Officer*

*Commissioner of Patents and Trademarks*

UNITED STATES PATENT AND TRADEMARK OFFICE
CERTIFICATE OF CORRECTION

PATENT NO. : 4,602,022

DATED : July 22, 1986

INVENTOR(S) : Paolo Cozzi, et al.

It is certified that error appears in the above-identified patent and that said Letters Patent is hereby corrected as shown below:

Column 1, lines 50-57, delete the structural formula in its entirety and insert therefor

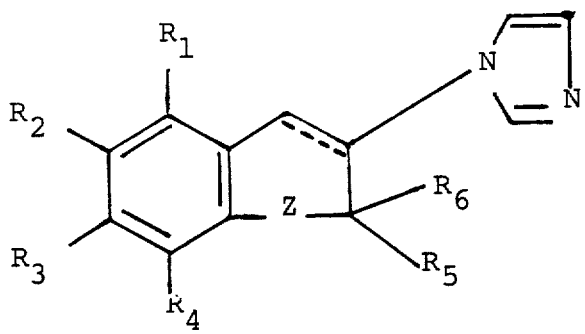

Signed and Sealed this

Twenty-first Day of April, 1987

Attest:

DONALD J. QUIGG

Attesting Officer

Commissioner of Patents and Trademarks